United States Patent

Mochizuki et al.

[11] Patent Number: 5,911,691
[45] Date of Patent: Jun. 15, 1999

[54] ULTRASOUND IMAGE PROCESSING APPARATUS AND METHOD OF FORMING AND DISPLAYING ULTRASOUND IMAGES BY THE APPARATUS

[75] Inventors: Takashi Mochizuki; Mutsuhiro Akahane; Masanori Hirose, all of Mitaka, Japan

[73] Assignee: Aloka Co., Ltd., Japan

[21] Appl. No.: 08/861,244

[22] Filed: May 21, 1997

Related U.S. Application Data

[63] Continuation-in-part of application No. 08/682,909, Jul. 16, 1996, Pat. No. 5,706,816.

[30] Foreign Application Priority Data

May 21, 1996 [JP] Japan .................................. P8-125342
May 21, 1996 [JP] Japan .................................. P8-125343

[51] Int. Cl.$^6$ ........................................................ A61B 8/00
[52] U.S. Cl. .......................................... 600/443; 128/916
[58] Field of Search .............................. 128/916; 600/443, 600/447

[56] References Cited

U.S. PATENT DOCUMENTS

| | | |
|---|---|---|
| 4,770,184 | 9/1988 | Greene, Jr. et al. . |
| 5,315,512 | 5/1994 | Roth . |
| 5,329,929 | 7/1994 | Sato et al. .............................. 128/916 |
| 5,379,769 | 1/1995 | Ito et al. . |
| 5,396,890 | 3/1995 | Weng . |
| 5,474,073 | 12/1995 | Schwartz et al. ...................... 128/916 |
| 5,488,952 | 2/1996 | Schoolman .............................. 128/916 |
| 5,497,776 | 3/1996 | Yamazaki et al. ...................... 128/916 |
| 5,669,385 | 9/1997 | Pesque et al. .......................... 128/916 |
| 5,682,895 | 11/1997 | Ishiguro .................................. 128/916 |
| 5,706,816 | 1/1998 | Mochizuki et al. .................... 128/916 |

FOREIGN PATENT DOCUMENTS

| | | |
|---|---|---|
| 0 476 495 A1 | 3/1992 | European Pat. Off. . |
| 0 487 339 A1 | 5/1992 | European Pat. Off. . |
| 0 612 502 A1 | 8/1994 | European Pat. Off. . |
| WO 91/03792 | 3/1991 | WIPO . |
| WO 96 00402 | 1/1996 | WIPO . |

Primary Examiner—Marvin M. Lateef
Assistant Examiner—Maulin Patel
Attorney, Agent, or Firm—Marger Johnson & McCollom, P.C.

[57] ABSTRACT

An image processing apparatus can display a tomographic image of an object in a three-dimensional region and a three-dimensional or stereoscopic image, such as a three-dimensional surface image of the object or a three-dimensional transparent image thereof, simultaneously on a screen. A sectional plane from which the tomographic image is produced is freely designated on the three-dimensional image displayed on the screen. The sectional plane can be indicated on the displayed three-dimensional image by a cursor line. Further, a data processing range along the ultrasound beam direction can be determined on the displayed tomographic image, in which the three-dimensional image is produced from the echo data obtained from the data processing range. Such a data processing range can also be indicated on the displayed tomographic image by means of cursor lines.

20 Claims, 12 Drawing Sheets

ULTRASOUND IMAGE PROCESSING APPARATUS AND METHOD OF FORMING AND DISPLAYING ULTRASOUND IMAGES BY THE APPARATUS

This application is a continuation-in-part of copending, commonly-assigned U.S. Ser. No. 682,909, filed Jul. 16, 1996, now U.S. Pat. No. 5,706,816, and priority is claimed from Japanese applications P8-125342 and P8-125343, both filed May 21, 1996.

BACKGROUND OF THE INVENTION

1. Field of the Invention

This invention relates to an ultrasound image processing apparatus and a method of forming and displaying ultrasound images by the apparatus, and in particular relates to an ultrasound image processing apparatus and a method of forming and displaying ultrasound images by the apparatus in which it is possible to produce in a real time base a three-dimensional image which represents an object such as an internal organ of a living body which can not be grasped from the outside thereof.

2. Description of the Background Art

As for image processing apparatuses which utilize ultrasound waves, there are known ultrasound diagnostic apparatuses, fault detectors, fish school detectors and sonar devices and the like. In these image processing apparatuses, ultrasound diagnostic apparatuses are used for diagnosing a living body, in which ultrasound waves are transmitted from a probe toward an object in a living body (e.g. an internal organ or a fetus or the like) and echoes of the ultrasound waves are received by the probe to obtain echo signals, and a tomographic image or the like is produced based on the echo signals to display it on a display or screen such as a CRT or the like.

In the meantime, recently, in the field of such ultrasound diagnostic apparatuses, various techniques have been proposed for obtaining a three-dimensional ultrasound image of an object by transmitting and receiving ultrasound waves to and from a three-dimensional region in which the object such as an internal organ or a fetus is positioned. According to these techniques, there is an advantage that the object can be grasped three-dimensionally or spatially through the three-dimensional ultrasound image.

However, in the prior art techniques, there is a problem that they require a fair amount of computing time for processing an enormous number of coordinate data to form a three-dimensional image. Therefore, it is impossible to obtain such a three-dimensional ultrasound image in a real time base, and therefore these apparatuses can not be practically used. Further, these prior art apparatuses can produce only a three-dimensional surface image of the object, and therefore they are not sufficient for carrying out diagnosis for the internal condition of the object. Such a problem can be seen not only in the ultrasound diagnostic apparatuses for medical use but also in ultrasound image processing apparatuses for use in other field such as sonars and fault detectors and the like.

In view of these problems involved in the prior art apparatuses, the inventors of this application have proposed in its co-pending U.S. application (Ser. No.: 08/682,909) a new ultrasound image processing apparatus which can be preferably used as ultrasound diagnostic apparatuses.

In this ultrasound image processing apparatus, ultrasound beams are emitted from an ultrasound probe toward a three-dimensional region in which an object such as an internal organ of a living body and a fetus or the like is placed while moving the ultrasound probe, and receiving echoes of the ultrasound beams which are reflected from the object. Echo data obtained from the received echoes are sequentially processed to form a three-dimensional ultrasound image (hereinafter, referred to as a "stereoscopic image") of the object in a real time. Further, in this ultrasound image processing apparatus, a new image processing technique which is developed from a volume rendering technique is employed, thereby enabling the apparatus to produce a transparent image of the inside of the internal organ (hereinafter, such a transparent image is referred to as "stereoscopic transparent image") in a real time base.

Therefore, according to the ultrasound image processing apparatus, there are advantages which could not be achieved by the prior art apparatus. Specifically, it is possible to obtain a stereoscopic image (a stereoscopic surface image or a stereoscopic transparent image) of the object in a real time, and it is also possible to grasp the surface condition of the internal organ being examined or the internal tissue structure thereof spatially by observing the stereoscopic surface image or stereoscopic transparent image which is displayed on a screen.

On the other hand, however, in a case where such an ultrasound image processing apparatus is utilized in an actual diagnosis for a living body, there is a case that the internal condition of the organ which is represented stereoscopically can not be grasped accurately. In order to diagnose the inside of such an organ, a tomographic image (B-mode image) is so far used, so that a diagnosing method using such a B-mode image has already been practically established.

Therefore, there is a demand for ultrasound image processing apparatuses which can perform not only an observation of the object through a stereoscopic ultrasound image such as a stereoscopic surface image or a stereoscopic transparent image but also an observation of the object through a B-mode image.

Further, when an internal organ or the like is observed by the ultrasound image processing apparatus, there is a problem that an observation is obstructed by another organ which is positioned in front of or in rear of the organ to be observed, because such other organ is likely to appear in the image displayed in the screen. For example, it is pointed out by doctors that when observing a fetus, a placenta which is positioned at a place closer to the body surface rather than the fetus is likely to appear on the displayed image.

SUMMARY OF THE INVENTION

This invention has been made in view of the problems involved in the prior art apparatuses. Accordingly, a main object of the present invention is to provide an ultrasound image processing apparatus which can display a three-dimensional image of an object placed in a predetermiend three-dimensional region together with a tomographic image (B-mode image) of the object simultaneously.

Another object of the present invention is to provide an ultrasound image processing apparatus in which the user can freely designate a position of a sectional plane which is to be represented through a tomographic image, on the displayed three-dimensional image.

Yet another object of the present invention is to provide an ultrasound image processing apparatus which can freely designate on the displayed tomographic image a data processing range in the three-dimensional region for which a three-dimensional image is to be produced.

Other object of the present invention is to provide an ultrasound image processing apparatus which is capable of improving a frame rate, that is a displaying speed, by appropriately changing ultrasound pulse transmission repetition frequency (PRF) in accordance with the designated data processing range having echo data from which the three-dimensional image is produced.

Yet other object of the present invention is to improve an accuracy of diagnosis by means of a three-dimensional image of an object to be diagnosed.

In order to achieve the main object of the present invention, an ultrasound image processing apparatus according to the present invention comprises:

(a) an ultrasound transducer for sequentially emitting ultrasound beams toward a three-dimensional region containing an object and receiving respective echoes of said ultrasound beams;

(b) three-dimensional image data producing means for producing in a substantially real time base stereoscopic image data of said object in said three-dimensional region based on echo data obtained from the echoes of said ultrasound beams;

(c) tomographic image data producing means for producing tomographic image data of said object based on the echo data; and (d) display means which can simultaneously display a three-dimensional image of the object formed from the three-dimensional image data and a tomographic image of the object formed from the tomographic image data.

According to the ultrasound image processing apparatus having the above structures, an object which is positioned in a three-dimensional region can be observed through a three-dimensional image or a tomographic image or through both images as necessary. In particular, in a case where the ultrasound image processing apparatus is applied to an ultrasound diagnostic apparatus for diagnosing a patient, it becomes possible to diagnose the patient by means of a three-dimensional image of an object to be diagnosed. The diagnosis using the three-dimensional image can be carried out taking the knowledge of the B-mode diagnosis which has already established practically into consideration. Further, if the B-mode image is displayed simultaneously together with the three-dimensional image when diagnosing the patient, it becomes possible to perform a novel unique diagnosis which could not be achieved by the prior art apparatuses, thereby enabling to perform more reliable diagnosis.

According to the present invention, it is preferred that the three-dimensional image and the tomographic image (B-mode image) are displayed simultaneously in a single display in a contrast manner.

Further, in this ultrasound image processing apparatus, it is also preferred that a tomographic image is taken along a sectional plane which is determined by a line freely designated on the displayed three-dimensional image.

In this case, the line can be indicated by a cursor on the displayed three-dimensional image. In order to display such a cursor line on the three-dimensional image, known means such as a trackball or a mouse can be used.

Furthermore, it is also preferred that two points spaced along the ultrasound beam direction are designated on the displayed tomographic image to determine a data processing range including the two points, and a three-dimensional image is produced based on the echo data contained in the data processing range. In this way, it becomes possible to display a three-dimensional image which is not affected by any obstructions which are positioned in front of or in rear of the designated data processing range.

In this case, the data processing range can be indicated on the displayed tomographic image using one or two cursor lines. In order to display these cursor lines on the tomographic image, known means such as a trackball or a mouse can be used.

Further, in this case, it is preferred that ultrasound pulse transmission repetition frequency (PRF) is changed appropriately in accordance with the depth of the data processing range, thereby enabling to improve a frame rate, that is a displaying speed of the image.

The present invention is also directed to a method of forming and displaying ultrasound images. The method comprises the steps of:

(a) transmitting ultrasound beams toward an object in a three-dimensional region and receiving echoes of the ultrasound beams;

(b) producing a three-dimensional image data of said object in said three-dimensional region in a real time base based on echo data obtained from the echoes of the received ultrasound beams;

(c) producing a tomographic image data of said object based on a part of the echo data of the received ultrasound beams; and (d) displaying a three-dimensional image which is formed based on the three-dimensional image data and a tomographic image which is formed based on the tomographic image data on a single display simultaneously such that these images are contrasted with each other.

In this method, it is preferable to include a further step of setting a sectional plane for the object at a desired location on the displayed three-dimensional image, wherein the tomographic image is formed from the echo data obtained from the sectional plane.

Further, it is also preferred to include a further step of determining a data processing range containing echo data to be processed based on the displayed tomographic image, wherein the three-dimensional image is produced from the echo data obtained from the range.

Furthermore, the present invention is also directed to a method of diagnosing a living body using ultrasound images. This method comprises the steps of:

(a) transmitting ultrasound beams toward a three-dimensional region of a living body and receiving echoes of the transmitted ultrasound beams;

(b) producing a three-dimensional image data of an object in said three-dimensional region in a real time base based on echo data obtained from the echoes of the ultrasound beams;

(c) producing a B-mode image along a desired sectional plane of the object based on a part of the echo data; and (d) displaying said three-dimensional image and said B-mode image simultaneously on a single screen in a contrast manner, thereby diagnosing the object based on the displayed images.

According to this diagnosing method, it becomes possible, when diagnosing the patient, to perform a novel unique diagnosis which could not be achieved in the prior art apparatuses, thereby enabling to perform more reliable diagnosis.

Other objects, functions and advantages of the present invention will be apparent when the following description of the preferred embodiments are considered taken in conjunction with the accompanying drawings.

THE PRINCIPLE OF THE REAL TIME STEREOSCOPIC IMAGE

Hereinbelow, a description is made with reference to the structure of the ultrasound image processing apparatus which produces the three-dimensional stereoscopic image (including three-dimensional surface image and three-dimensional transparent image) used in the present invention as well as the principle for producing such a three-dimensional image.

(1) Structure of the Apparatus

Figure 1:
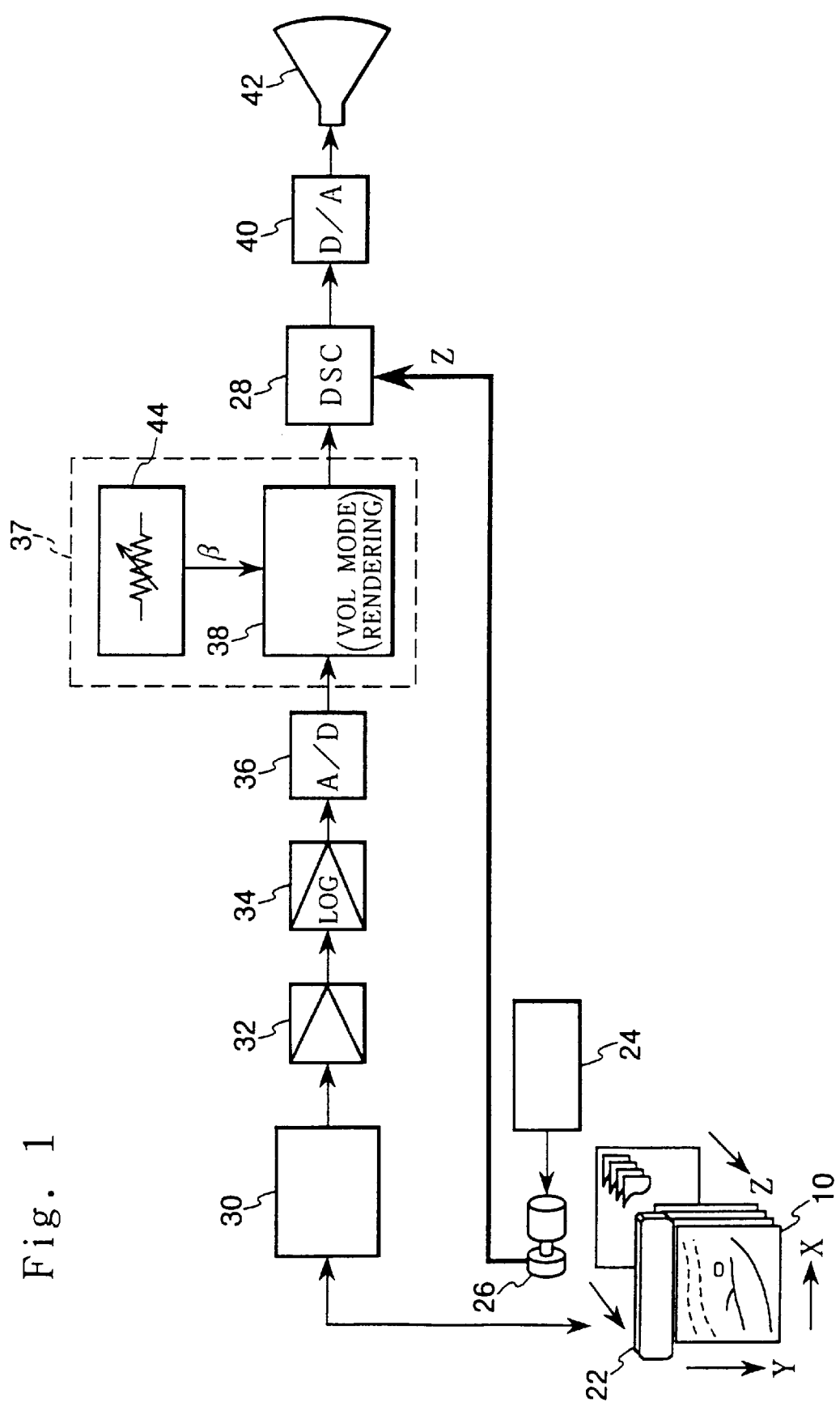
FIG. 1 is a block diagram which shows the overall structure of an ultrasound image processing apparatus which can produce a three-dimensional image in a real time base.

FIG. 1 is a block diagram illustrating the overall structure of an ultrasound image processing apparatus for producing the three-dimensional image.

In FIG. 1, the reference numeral 22 denotes an ultrasound probe which comprises a transducer for emitting ultrasound beams toward a three-dimensional region such as a living body and for receiving the beams (echoes) that are reflected from an object in the three-dimensional region such as an internal organ of the living body or a fetus or the like. In this embodiment, the ultrasound probe 22 has a linear type array transducer.

Figure 2B:
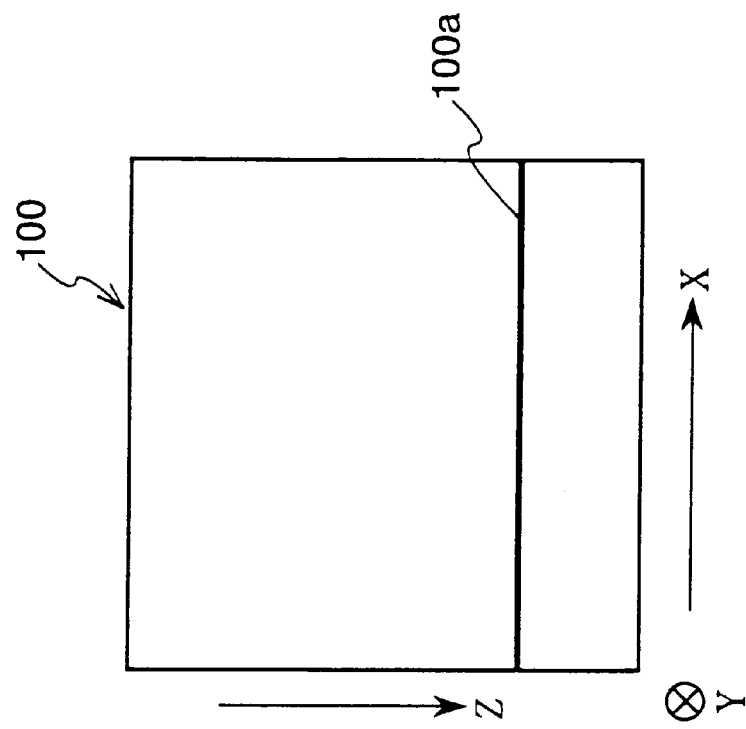
FIG. 2B is an illustration which explains a three-dimensional ultrasound image obtained by the above ultrasound image processing apparatus.
Figure 2A:
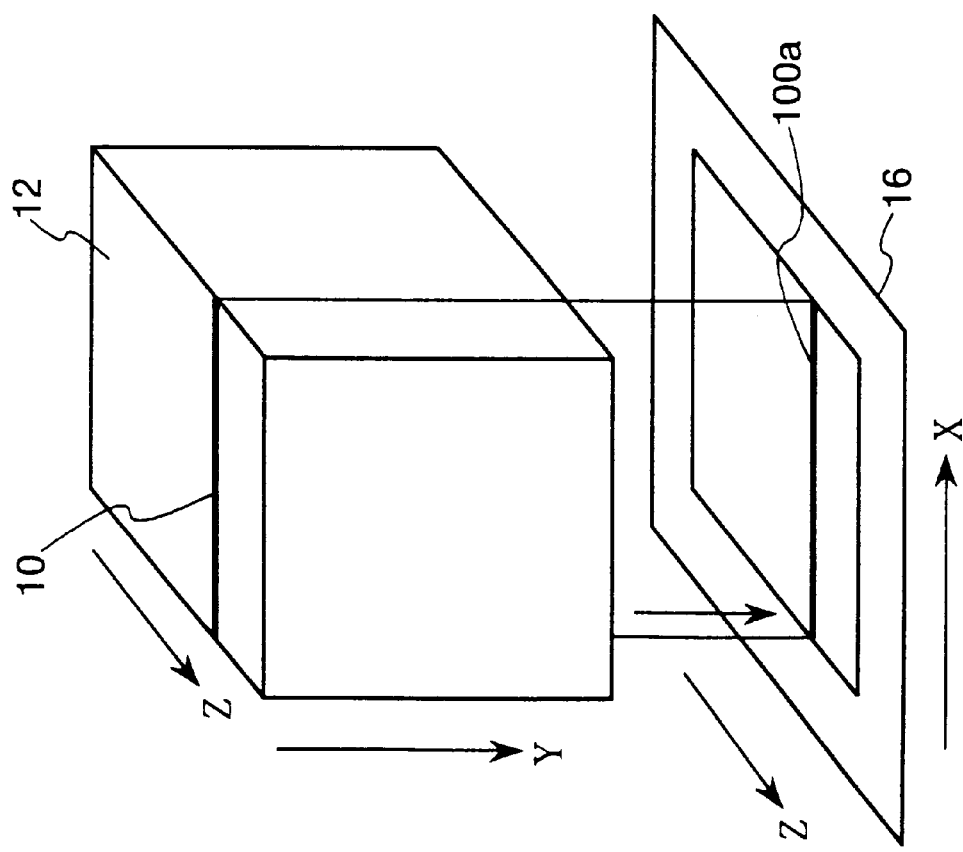
FIG. 2A is an illustration which explains a relationship between a three-dimensional region and a projected image.

By electronically scanning the linear array transducer of the ultrasound probe 22, a scanning plane 10 is formed in an X-Y plane as shown in FIG. 2A. Further, by mechanically scanning the ultrasound probe 22 in the Z direction, the scanning plane 10 is displaced in the Z direction, thereby forming a three-dimensional echo data acquiring region 12 as shown in FIG. 2A (hereinafter, referred to as "three-dimensional region").

In this embodiment, such a mechanical scanning is carried out through a driving device 24. During the mechanical scanning, a rotary encoder 26 continuously detects a position of the ultrasound probe 22 in the Z direction and produces Z coordinate data for the ultrasound probe 22. This Z coordinate data is fed to a digital scan converter (DSC) 28 (described later), and the Z coordinate data is used in the DSC 28 for writing brightness value data of respective ultrasound beams in a frame memory provided therein.

By mechanically scanning the ultrasound probe 22 in the Z direction while emitting ultrasound beams toward the three-dimensional region 12 and receiving echoes of the ultrasound beams sequentially, it is possible to obtain echoes from the three-dimensional region 12.

In this embodiment, a description is made with reference to a case where the ultrasound probe 22 is mechanically driven in the Z direction by means of the driving device 24. However, it goes without saying that the ultrasound probe 22 can be moved manually by an operator to perform a scanning in the Z direction. In this case, it is also necessary to acquire a Z coordinate data of the ultrasound probe 22 using an appropriate means.

In addition, although in this embodiment an ultrasound probe 22 having a linear array transducer is used, it is also possible to use other types of ultrasound probes having a convex type array transducer or a sector type array transducer or the like. Examples of such an ultrasound probe is disclosed, for example, in U.S. Pat. No. 5,460,179 and U.S. Pat. No. 5,152,294. In a case where these ultrasound probes are used, the Z coordinate data, that is, the yawing angle data of the probe, is sent to the digital scan converter (DSC) 28.

Turning now to FIG. 1, a signal transmission and reception section 30 supplies a transmission signal to the ultrasound probe 22 to energize the transducer to emit ultrasound beams. The signal transmission and reception section 30 also receives echo signals produced based on echoes of the reflected beams received by the transducer of the ultrasound probe 22. The echo signals outputted from the signal transmission and reception section 30 are first amplified by an amplifier 32, and then they are logarithmically amplified by a LOG amplifier 34. The LOG amplifier 34 is provided in order to improve the quality of an ultrasound image. An A/D converter 36 converts the echo signals into digital signals. Then, the converted digital signal (hereinafter, referred to as "echo data") are sent to a stereoscopic (three-dimensional) image data generator (stereoscopic image data producing section) 37.

The stereoscopic image data generator 37 comprises an image processor 38 as a transparent image data generator. The stereoscopic image data generator 37 processes echo data obtained from the received echoes of the respective ultrasound beams sequentially to ultimately produce brightness value data for the respective ultrasound beam each time when the echo of the respective ultrasound beam emitted to the three-dimensional region is received (This will be described later in further detail with reference to FIG. 7). The thus-produced brightness value data of the respective ultrasound beam is used as a brightness value P(x,y) of a pixel in an ultrasound image. Therefore, the pixel is designated so as to correspond to the ultrasound beam of which echo data has been processed.

Further, the image processor 38 is constructed so as to receive an opacity adjustment coefficient β determined by the opacity adjuster 44 (This will also be described later in further detail). An appropriate selection of the value for the opacity adjustment coefficient β allows the opacity α at each sampling point (voxel) in a beam direction to be set as desired.

The brightness value data thus obtained by the stereoscopic image data generator 37 corresponding to respective ultrasound beam is sequentially outputted to the DSC 28 each time upon such a brightness value data being produced, and then written into predetermined addresses of the frame memory in the DSC 28 in a predetermined order. Namely, this frame memory has X-Y addresses corresponding to the pixels of a display or screen for displaying an ultrasound image on one-to-one basis. Therefore, a series of the brightness value data of the respective ultrasound beams projected toward the three-dimensional region are made to be written sequentially into corresponding predetermined addresses, respectively. As a result, upon completing a scan for the three-dimensional region, the frame memory of the DSC 28 stores the brightness value data (scan data) of the ultrasound beams projected toward the three-dimensional region, that is, ultrasound image data for a single frame of a three-dimensional or stereoscopic ultrasound image.

In this case, as described above, the respective ultrasound beams are identified by X-Z coordinates, and the brightness value data for the respective ultrasound beams are written into corresponding predetermined X-Y addresses in the frame memory, respectively (Refer to FIG. 2A and FIG. 2B.).

Ultrasound image data read from the DSC 28, after having been converted by a D/A converter 40 into analog signals, are sent to a display or screen 42 such as a CRT. Then, the display 42 displays a three-dimensional or stereoscopic ultrasound image according to the present invention.

(2) Generation of Real Time Three-dimensional Image

Hereinbelow, a descriptions is made with reference to a production of real time three-dimensional image.

As stated above, FIG. 2A is an illustration which shows a relationship between a three-dimensional region 12 and a projected image.

As shown in FIG. 2A, when an ultrasound beam emitted in the Y direction is scanned in the X direction, a scanning plane 10 is formed on the X-Y plane. Further, when the scanning plane 10 is moved in the Z direction to perform a mechanical scan, a three-dimensional region 12 (a three-dimensional echo data acquiring region) is produced.

Each time upon a receipt of the echo of an ultrasound beam projected toward the three-dimensional region 12, an image processing operation for generating brightness value data for the ultrasound beam is carried out. If the thus-obtained brightness value data for all the ultrasound beams which have been sequentially projected toward the three-dimensional region are plotted on a mapping plane 16 (i.e. an X-Z plane 16) which is virtually set as a plane on which the ultrasound beams passing through the three-dimensional region 12 are projected, an ultrasound image for the three-dimensional region is formed on the mapping plane. The ultrasound image corresponds to a stereoscopic ultrasound image which can be obtained by the ultrasound image processing apparatus according to the present invention.

FIG. 2B is an illustration which explains a three-dimensional ultrasound image obtained according to the present invention. Namely, by performing image data processing as described above for each of the echo data of the ultrasound beams which have been emitted toward the three-dimensional region 12, an ultrasound image 100 shown in FIG. 2B is obtained based on the brightness value data for the respective ultrasound beams.

Namely, the above described processing is sequentially executed for the echo data for each of all the ultrasound beams emitted toward the three-dimensional region 12. As a result, based on the brightness value data for the respective ultrasound beams, a single frame of an ultrasound image 100 for the three-dimensional region 12 is formed. The thus-formed ultrasound image 100 is considered to be equivalent to the image plotted on the mapping plane 16 as shown in FIG. 2B. Namely, in the ultrasound image 100, one [1] line 100a in the X direction corresponds to a single scanning plane 10. Further, the number of plots on the mapping plane 16 matches the number of ultrasound beams. This means that each of the ultrasound beams corresponds to one [1] pixel in the ultrasound image 100. In other words, one [1] ultrasound beam projected to the three-dimensional region corresponds to one [1] pixel in the ultrasound image 100.

The ultrasound image 100 is similar to an image obtained by viewing the three-dimensional region from a point from which the ultrasound beams are emitted. Thus, when the point of emitting the ultrasound beams is taken as a viewpoint, each of the ultrasound beams can be taken as a line of vision. This enables the diagnosed part (three-dimensional region) to be observed as if it is observed by the naked eye.

Figure 3:
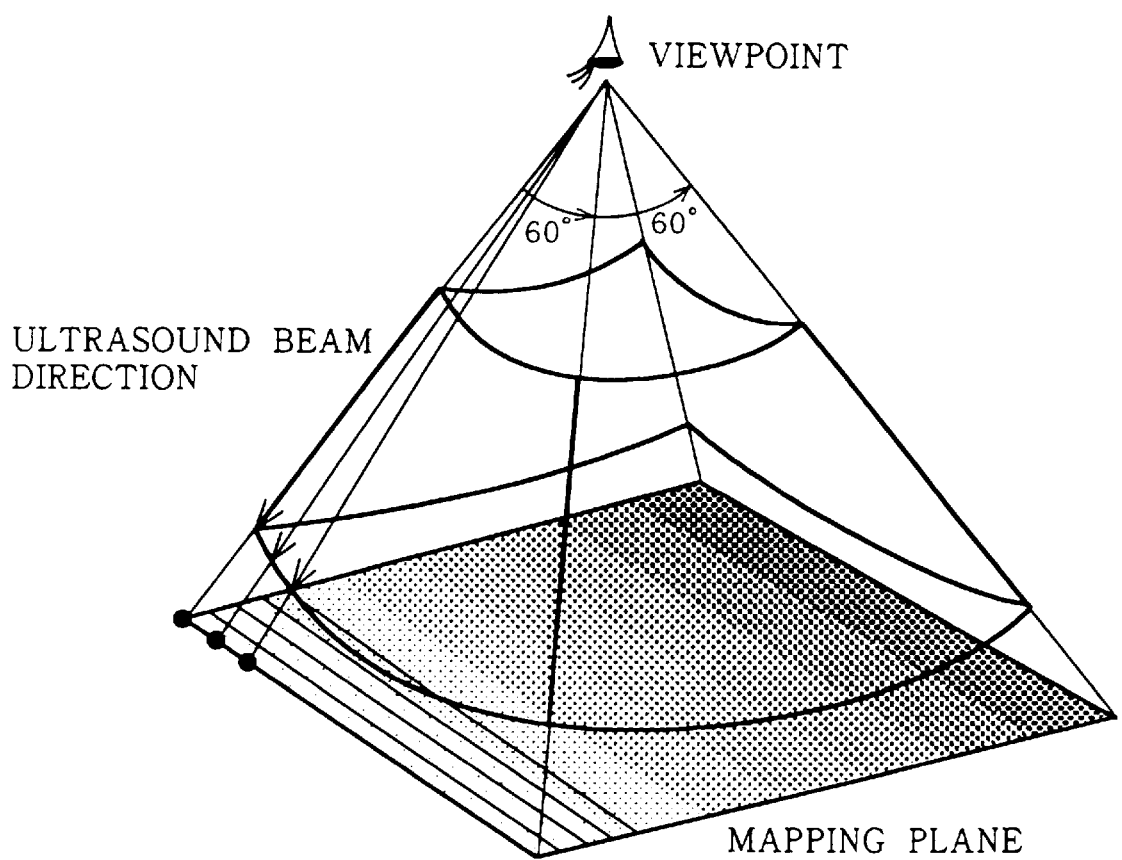
FIG. 3 is another illustration which explains a relationship between a three-dimensional region and a projected image.

FIG. 3 is an illustration which shows another relationship between a three-dimensional region 12 and a projected image. Specifically, in the case shown in FIG. 3, a scan is performed for a three-dimensional region by an ultrasound probe having a convex type array transducer such as the one disclosed in the above-mentioned U.S. patents.

More specifically, as shown in the drawing, the position of the ultrasound probe having a convex type array transducer is set at a position that is considered to be a viewpoint with respect to the three-dimensional region (an object), from which ultrasound beams are emitted toward the three-dimensional region. In this array transducer, ultrasound beams emitted from the both ends thereof define an angle of sixty [60] degrees to form a scanning plane therebetween. Further, the array transducer is swung through an angle of sixty [60] degrees to perform a mechanical scan. In this way, a scan is performed for the three-dimensional region.

During the scanning, the array transducer sequentially emits ultrasound beams toward the three-dimensional region and receives their echoes reflected therefrom. The received echoes are sequentially processed as described above to generate brightness value data for the respective ultrasound beams. In the same manner as with the case shown in FIG. 1 in which an ultrasound probe 22 having a linear type array transducer is used, the brightness value data for each of the ultrasound beams corresponds to a brightness value at a corresponding pixel of an ultrasound image which is plotted on a mapping plane which is virtually set as a plane on which the ultrasound beams passing through the three-dimensional region are projected. In this case shown in FIG. 3, the number of pixels in the ultrasound image matches the number of ultrasound beams.

As described above, in the ultrasound image obtained according to the present invention, the directions of the ultrasound beams match the directions of lines of vision for image rendering. In other words, the ultrasound image is equivalent to an image which would be obtained by using an ultrasound beam as a line of vision. Therefore, it is possible to produce a three-dimensional ultrasound image which is substantially the same as an image obtained by viewing the three-dimensional region (object) from a viewpoint from which the ultrasound beams are emitted.

Further, because the echo data for the respective ultrasound beams is processed each time the echo of the ultrasound beam is received, it is possible to produce brightness value data for the respective ultrasound beams sequentially. With this result, an ultrasound image of the already scanned part of the three-dimensional region can be produced almost simultaneously with the displacement (scan) of the ultrasound probe. This, in turn, allows an ultrasound image of the three-dimensional region to be produced almost simultaneously with a completion of the displacement (scan) of the probe. This eliminates the necessity for recording an enormous amount of three-dimensional data in a memory such as a geometry memory and rereading the same out from the memory for an image production, thereby making it possible to produce a three-dimensional or stereoscopic ultrasound image for the three-dimensional region on real time basis.

In this way, it is possible to greatly reduce a time required for producing a three-dimensional image. Further, since no additional echo data memory such as a geometry memory is necessary, it is possible to reduce the number of parts and thereby provide a practical ultrasound diagnostic apparatus capable of producing a stereoscopic (three-dimensional) ultrasound image at a relatively low cost.

(3) Generation of Three-dimensional or Stereoscopic Transparent Image—Volume Rendering Hereinbelow, a description is made with reference to the principle of Volume Rendering technique used in production of three-dimensional or stereoscopic transparent image. This is carried out by the stereoscopic image data generator 37, the image processor 38 and the opacity adjuster 44 shown in FIG. 1.

As described earlier, according to the present invention, it is possible to display not only a stereoscopic surface image of an object placed in a three-dimensional region but also a stereoscopic transparent image of the object like an X-ray image as necessary (called as "Vol-mode image" by the inventors). The data used for producing such a three-dimensional images is generated by applying a volume rendering technique used in the field of computer image processing to an ultrasound image processing with the characteristics specific to ultrasound waves in mind. Thus, the principle underlying volume rendering is explained first with reference to FIG. 4, FIG. 5 and FIG. 6.

Figure 4:
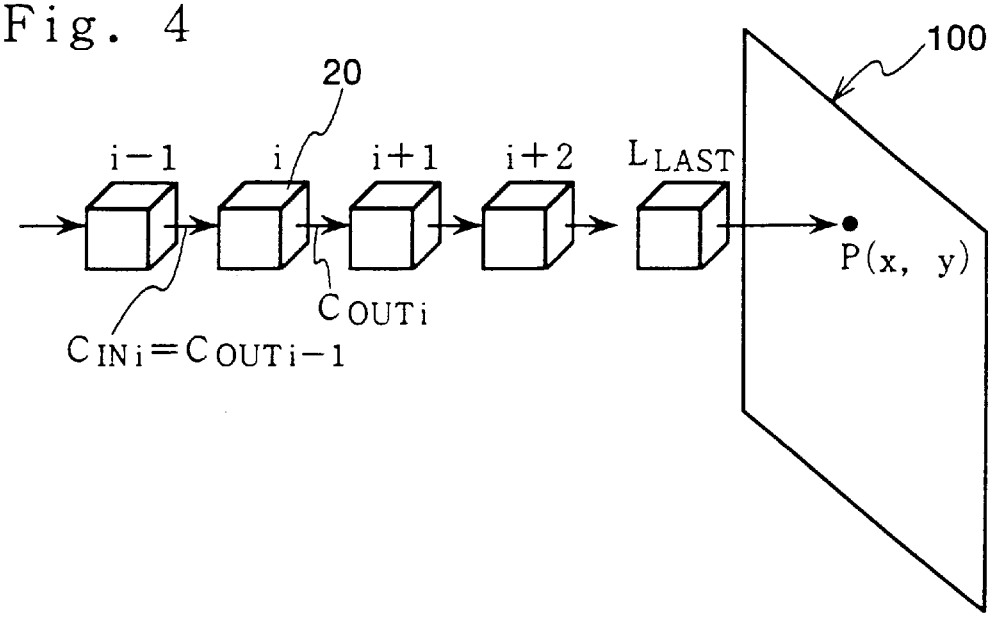
FIG. 4 is an illustration which shows a relationship between a quantity of inputted light and a quantity of outputted light at each voxel 20.
Figure 5:
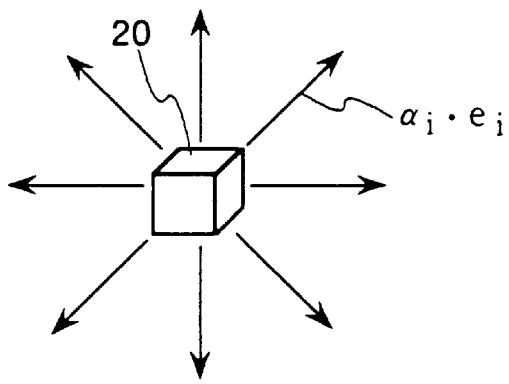
FIG. 5 is an illustration which explains a quantity of luminescence at each voxel 20.

In these drawings, FIG. 4 is an illustration for explaining a relationship between a quantity of inputted light and a quantity of outputted light at each voxel 20, and FIG. 5 is an illustration for explaining a quantity of luminescence at each voxel 20.

More specifically, FIG. 4 and FIG. 5 show the concept of a voxel 20. Here, it should be noted that one [1] voxel 20 corresponds to one [1] echo data which is obtained by A/D converting an echo signal obtained from an echo of an ultrasound beam. In other words, a voxel 20 is defined as a volume element at one of a plurality of sampling points. The sampling point is determined in correspondence with one [1] cycle of the A/D conversion rate of the A/D converter 36 (shown in FIG. 1) operating in synchronization with a sampling clock, as described later in further detail. That is, the voxel 20 can be understood as each one of a plurality of sampling points positioned along the beam projecting direction. Hereinbelow, echo data at each voxel is referred to as "normalized echo data".

Therefore, in the application of the volume rendering technique to the ultrasound image processing apparatus, an ultrasound beam is considered to be a series of a number of voxels, and an ultrasound wave is assumed to be equivalent to light. In other words, in the present invention, echoes of ultrasound waves are visualized as an image on the assumption that the ultrasound waves would be substituted by light.

FIG. 4 shows respective voxels 20 i–1 through $L_{LAST}$. A value obtained by processing a number of voxels of an ultrasound beam sequentially from the first (initial) voxel 20 corresponds to a brightness value P(x,y) of one [1] pixel in the ultrasound image 100 on a display screen.

Here, in accordance with the volume rendering technique, an opacity α and a transparency (1–α) are defined for each voxel 20. In this case, the opacity α correlates with the voluntary luminescence of light at a voxel 20 to its surroundings as shown in FIG. 5. On the other hand, the transparency (1–α) correlates with the transmission rate of an ultrasound wave at a voxel 20 transmitted from the immediately preceding voxel 20. In this embodiment, the opacity α is set in a range between zero [0] and one [1]. That is, $0 \leq \alpha \leq 1$. In the present invention, the opacity α is defined as a function of echo data (normalized echo data), and therefore it can be represented, for example, by the following Equation (1):

$$\alpha = \beta \times e^{\gamma} \qquad (1)$$

Here, e represents a value (size) of echo data (normalized echo data), and β is a constant (an opacity adjustment coefficient). As for γ, a value preferably greater than one [1], for example, two [2] or three [3], is substituted. As a result, the opacity α varies nonlinearly with respect to the value e of the normalized echo data. This means that the opacity α varies in response to the value (size) of the normalized echo data. In this case, the value (size) of the opacity α correlates with difusion/scattering of ultrasound wave to surroundings. Further, the value (size) of the transparency (1–α) correlates with tranmission rate of the ultrasound wave. In this case, the constant β is set so as to be variable.

As shown in FIG. 4, for an i-th voxel 20, a quantity of inputted light $C_{INi}$ and a quantity of outputted light $C_{OUTi}$ are defined. In this case, its quantity of inputted light $C_{INi}$ is equal to a quantity of outputted light $C_{OUTi-1}$ an (i–1)-th voxel 20 that immediately precedes the i-th voxel 20. Thus, this relationship can be represented by the following Equation (2):

$$C_{INi} = C_{OUTi-1} \qquad (2)$$

Here, it should be noted that that $C_{INi}=0$ for a first voxel.

For each voxel, based on the above-described opacity α and transparency (1–α), a quantity of luminescence and a quantity of transmitted light are defined. Thus, a quantity of luminescence of i-th voxel 20 is defined as a product between an opacity $\alpha_i$ and normalized echo data $e_i$, that is, $\alpha_i \times e_i$. Further, a quantity of transmitted light of i-th voxel 20 is defined as a product of a transparency $(1-\alpha_i)$ and a quantity of inputted light $C_{INi}$, that is, $(1-\alpha_i) \times C_{INi}$. In this case, the quantity of luminescence corresponds with the degree of contribution of the voxel 20 to a brightness value P(x,y) of the ultrasound beam at the corresponding pixel. Further, the value of a quantity of transmitted light corresponds to transmission rate of an ultrasound wave at a i-th voxel 20, when the voxel is considered as a transfer medium of an ultrasound wave. Thus, if the value of the transparency $(1-\alpha_i)$ at a voxel 20 is greater, ultimate contribution of the echo data of the voxel 20 to the brightness value P(x,y) also becomes greater.

Figure 6:
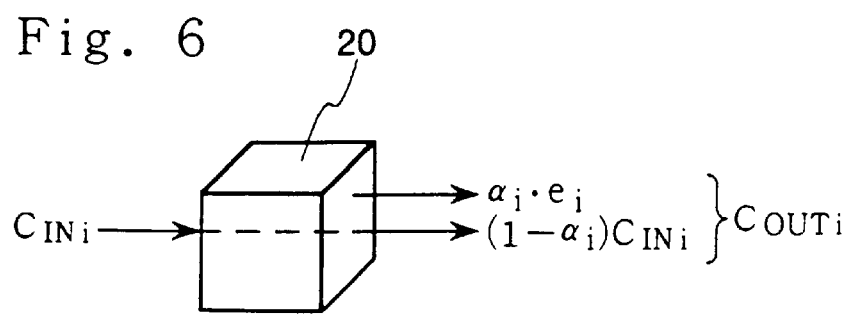
FIG. 6 is an illustration which explains a quantity of outputted light at each voxel 20.

FIG. 6 is an illustration which shows a quantity of outputted light at each voxel 20. As shown in FIG. 6, in the present invention the quantity of luminescence $\alpha_i \times e_i$ and the quantity of transmitted light $(1-\alpha_i) \times C_{INi}$ at an i-th voxel 20 are added together as shown in the following Equation (3), to determine a quantity of outputted light $C_{OUTi}$ at the i-th voxel 20.

$$C_{OUTi} = (1-\alpha_i) \times C_{INi} + \alpha_i \times e_i \qquad (3)$$

In Equation (3), it is to be noted that, from Equation (2), $C_{INi} = C_{OUTi-1}$. This means that the result of computing the quantity of outputted light at a preceding voxel is used in computing one at the current voxel.

While processing is carried out for a first voxel and its succeeding voxels sequentially in accordance with Equation (3), the opacity $\alpha_i$ at each of the voxels 20 is summed. Further, when its sum $\Sigma \alpha_i$ reaches one [1], the processing can be ended. Here, the processing also ends when the processing reaches the voxel $L_{LAST}$ which is the last voxel or a voxel which corresponds to a preset depth. That is, an end determining condition for the processing is represented by the following Equation (4):

$$\Sigma \alpha_i = 1 \text{ or } i = L_{LAST} \qquad (4)$$

The end of processing upon satisfying the end determining condition $\Sigma \alpha_i = 1$ in Equation (4) means that the processing is terminated when the cumulative value of the opacity $\alpha_i$ at each of the voxels 20 reaches one [1]. Of course, it is possible to change the end determining condition of Equation (4) so as to meet a particular situation. For example, a predetermined end determining value K, which is one [1] in this case, for setting a maximum of the sum $\Sigma \alpha_i$ may be changed to some other number.

In this embodiment, the quantity of outputted light $C_{OUTi}$ at the voxel 20 at a time when the end determining condition is satisfied is considered to be the brightness value data of the ultrasound beam, that is, the brightness value P(x,y) at the corresponding pixel in an ultrasound image. Then, the above-described processing is also carried out for the echo data for subsequently received ultrasound beams. Such processing is continued until it is completed for all the ultrasound beams emitted to a three-dimensional region.

As expressed in Equation (3), the brightness value P(x,y) at the pixel in the ultrasound image on a display screen reflects the values of all normalized echo data e of an ultrasound beam from a first voxel to a voxel judged to be an end. However, unlike a mere simple cumulative value of echo data as in the prior art described above, the brightness value obtained in accordance with the present invention reflects both scattering (diffusion) and absorption of an ultrasound wave at respective voxels. Accordingly, it is possible to effectively produce a stereoscopic transparent ultrasound image having a feeling of depth (a stereoscopic feeling) and a transparency like an image formed by a light emitted from a light source and transmitted through respective voxels with scattering and absorption. Further, it is also possible to visualize a part having an unclear boundary, that is, a boundary of tissues whose acoustic impedances are not so distinct from each other.

In connection with the application of the volume rendering technique to the present invention, it is to be noted that an image processing technology utilizing such a volume rendering technique has already been adopted in an X-ray CT apparatus. (Refer, for example, to IEEE Computer Graphics and Applications, Volume 8, Number 5, May 1988, pages 29–37.) However, since an X-ray CT apparatus detects an object with quantitative CT values irrespective of the direction of a projected X-ray, it is not possible to produce a three-dimensional image by using the detected data as they are. For this reason, in the X-ray CT apparatus, in order to produce a three-dimensional image, it is necessary to preset a virtual light source (viewpoint) and then process the detected data, on the assumption that the object is viewed from the viewpoint, by using a complex algorithm.

In contrast with the X-ray CT apparatus, in apparatuses using ultrasound waves, there are the following features. Namely, in the case of ultrasound waves, a relatively strong echo is obtained from a plane perpendicular to an ultrasound beam direction, while a relatively weak echo is obtained from a plane inclined with respect to the ultrasound beam direction. Further, a reflection from a hard part produces a strong echo, while a reflection from a soft part produces a weak echo.

Consequently, in image processing apparatuses using ultrasound waves having the above properties, obtained data, that is, the normalized echo data, reflect the feature and characteristic of a tissue as well as the direction of an ultrasound beam with respect to an object, namely, an angle formed between the direction of a line of vision and the surface of an object. Therefore, in image processing apparatuses using ultrasound waves, it is possible to easily produce an image having a stereoscopic effect (a depth feeling) by using the obtained echo data as they are. Namely, the application of a volume rendering technique to ultrasound image processing apparatuses has the advantage that it is possible to easily produce, with a relatively simple algorithm, a stereoscopic transparent image having a depth feeling that has never been attained by the prior art apparatuses or methods.

(4) Circuit Configuration for Volume Rendering

Figure 7:
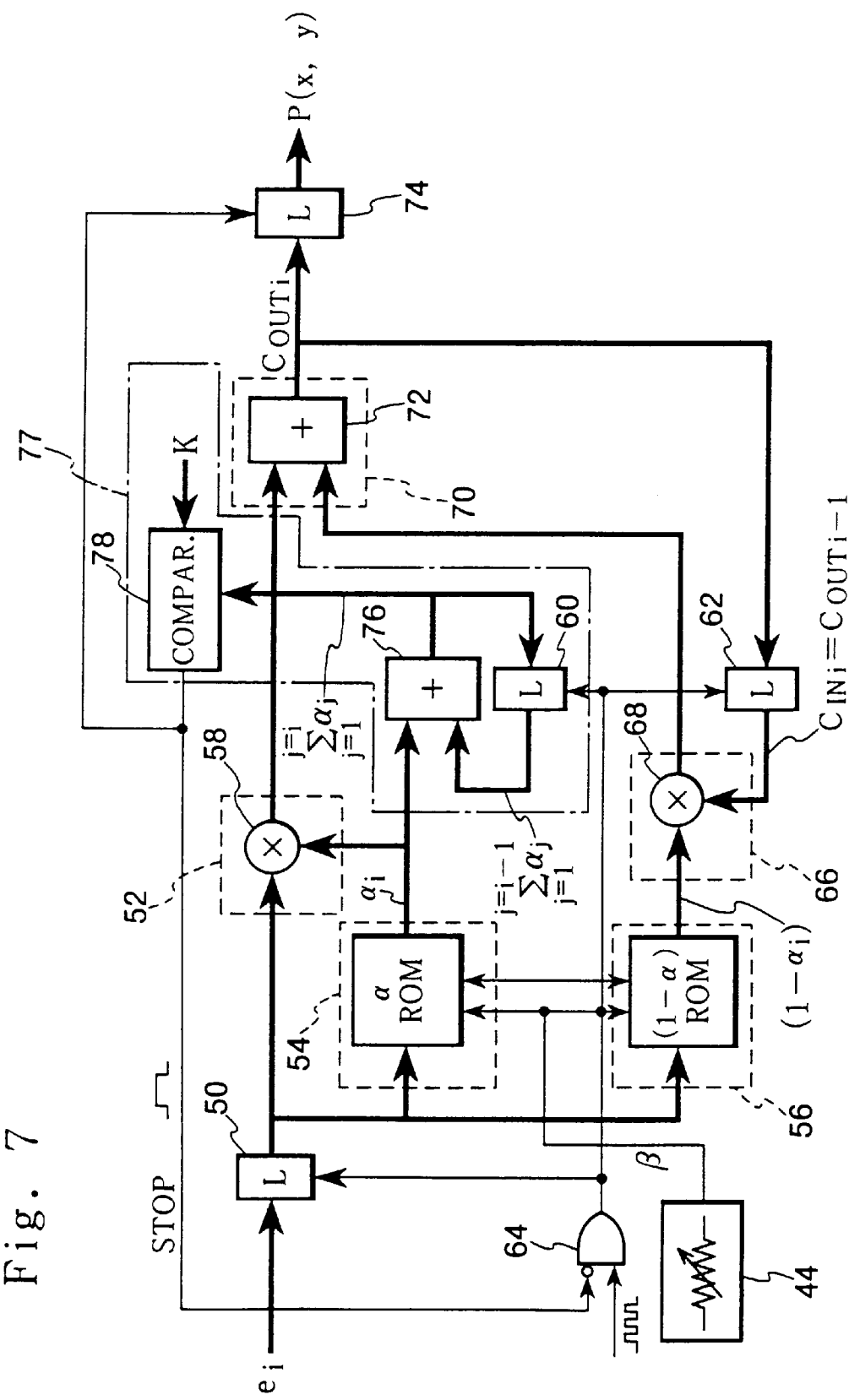
FIG. 7 is a block diagram which illustrates an example of the three-dimensional image data processing section shown in FIG. 1.

FIG. 7 is a block diagram illustrating a concrete example of a circuit configuration of the image processor 38 shown in FIG. 1. As shown in FIG. 7, normalized echo data $e_i$ at an i-th voxel 20 which has already been A/D converted is sequentially inputted to the image processor 38. The inputted echo data $e_i$ is first latched by a latch circuit 50, and then it is inputted to a luminescence quantity operator 52, an opacity operator 54 and a transparency operator 56, respectively. The luminescence quantity operator 52 comprises a multiplier 58. The multiplier 58 calculates the luminescence quantity as a product $e \times \alpha$ by multiplying normalized echo data e by an opacity $\alpha$ at each voxel 20. In this embodiment, the opacity operator 54 comprises an $\alpha$ ROM. The $\alpha$ ROM includes a table having data concerning a correspondence relationship between the normalized echo data e and the opacity $\alpha$ at each voxel 20. Similarly, the transparency operator 56 comprises a $(1-\alpha)$ ROM, which includes a table having data concerning a correspondence relationship between the normalized echo data e and the transparency $(1-\alpha)$ at each voxel 20.

Consequently, when the normalized echo data $e_i$ of an i-th voxel 20 is inputted into the opacity operator 54, the opacity operator 54 outputs opacity $\alpha_i$ at the voxel 20. Further, when the normalized echo data $e_i$ of the i-th voxel 20 is inputted into the transparency operator 56, the transparency operator 56 outputs transparency $(1-\alpha_i)$ at the voxel 20.

The opacity operator 54, the transparency operator 56, the latch circuit 50, a latch circuit 60 and a latch circuit 62 are all supplied via an AND gate 64 with a sampling clock. This sampling clock is also supplied to the A/D converter 36 shown in FIG. 1 for an A/D conversion. As a result, this sampling clock causes other circuits shown in FIG. 7 to operate in synchronization with the A/D converter 36. This enables normalized echo data e at each sampling point, that is, normalized echo data e at each voxel 20, to be processed sequentially.

The output of the transparency operator 56 is supplied to a transmitted light quantity operator 66 which comprises a multiplier 68. The multiplier 68 multiplies a transparency $(1-\alpha_i)$ outputted from the transparency operator 56 by a quantity of outputted light $C_{OUTi-1}$ of the immediately preceding (i−1)-th voxel 20 latched by latch circuit 62. Namely, the transmitted light quantity operator 66 outputs a quantity of transmitted light as a product $C_{INi} \times (1-\alpha_i)$ by multiplying a quantity of inputted light $C_{INi}$ of the i-th voxel by a transparency $(1-\alpha_i)$ at the voxel 20.

A light quantity adder 70 which is constructed from an adder 72 adds the quantity of luminescence to the quantity of transmitted light based on Equation (3), to output the sum as a quantity of outputted light $C_{OUTi}$ at the i-th voxel 20. The quantity of outputted light $C_{OUTi}$ outputted from the light quantity adder 70 is supplied to a latch circuit 74 having a gate function and the latch circuit 62, respectively. That is, the quantity of outputted light at an i-th voxel 20 is fed back via the latch circuit 62 to the transmitted light quantity operator 66 for computing a quantity of outputted light at an immediately succeeding (i+1)-th voxel 20.

An end determination section 77 determines an end of the above-described processing performed along the projecting direction of an ultrasound beam, that is, a series of voxels. More specifically, the end determination section 77 comprises an adder 76, a latch circuit 60 and a comparator 78. The adder 76 sequentially receives opacity $\alpha$ of respective voxels 20 as its input, while the adder 76 receives at its other input terminal an output from the adder 76 in a fed back manner via the latch circuit 60. This configuration allows the adder 76 to output from its output terminal a cumulative value $\Sigma\alpha_i$, which is the sum of the opacity $\alpha$ at each of voxels 20 summed sequentially from one at a first voxel 20.

The comparator 78 compares the cumulative value $\Sigma\alpha_i$ with a predetermined end determination value K. And when both values match, the comparator 78 outputs an end determination pulse. More specifically, the end determination section 77 outputs an end determination pulse when the cumulative value $\Sigma\alpha_i$, which is obtained by adding the opacity $\alpha$ of the respective voxels sequentially, reaches the predetermined end determination value K. The value K is usually set to one [1].

The end determination pulse is supplied to the AND gate 64 after having been inverted by an inverter at one of its input terminals, and the end determination pulse halts a pass-through of the sampling clock. Further, the end determination pulse is also supplied to the latch circuit 74 to release a latch of a quantity of outputted light $C_{OUTi}$ of the voxels 20 outputted from the light quantity adder 70.

The quantity of outputted light $C_{OUTi}$ becomes the brightness value data of the ultrasound beam which corresponds to a brightness value P(x,y) at a pixel in an ultrasound image on a display screen. In this regard, it is to be noted that the pixel holds brightness value P(x,y) for the corresponding ultrasound beam whose echo data has been processed as described above. The thus-generated brightness value data is then fed to the DSC 28 sequentially. In the DSC 28, the brightness value data for each of the ultrasound beams is sequentially stored in a predetermined address of a frame memory.

As previously described, not only when the above processing has been carried out for all the voxels including the last voxel 20 of an ultrasound beam, but also when the above processing has been carried out for the respective voxels preceding the voxel 20 corresponding to a preset depth along the beam direction, the end determination section 77 also halts processing echo data, in a manner similar to that described above. Namely, the end determination section 77 determines an end of processing, when processing reaches a voxel at a preset depth (or the final voxel), or when the sum $\Sigma\alpha_i$ of an opacity $\alpha_i$ at respective voxels 20 summed sequentially from one at a first voxel 20 reaches the predetermined end determination value K, which is usually set to one [1].

Consequently, in the case where respective values of opacity $\alpha$ of voxels on an ultrasound beam (a line of vision) which are to be sequentially added are large enough, the end determination section 77 halts the processing in a relatively early stage, to produce, for example, a transparent image only as far as the tissue surface, instead of deep into tissue entrails. In other words, if an opacity varying unit for varying the value of opacity is further provided, it is possible to set a desired value to the opacity $\alpha$ with respect to the normalized echo data e, which is used as a variable factor in the end determining condition of the end determination section 77.

In this way, it becomes possible to change the displayed three-dimensional image of the object from the three-dimensional transparent image of the object to the three-dimensional surface image thereof as necessary by adjusting or varying the value of opacity appropriately.

As described above, according to the circuit configuration shown in FIG. 7, sequential processing for voxels 20 in each of a plurality of ultrasound beams starts from the first voxel 20 along the beam projecting direction. Therefore, a quantity of outputted light $C_{OUTi}$ at an i-th voxel 20 outputted from the quantity of light quantity adder 70 is sequentially used for computing a quantity of outputted light $C_{OUTi+1}$ at an immediately succeeding (i+1)-th voxel 20 in a feedback manner. In other words, in computing a quantity of outputted light $C_{OUTi}$ at an i-th voxel 20, the echo data of the preceding voxels are reflected thereto. As a result, in the brightness value data of the ultrasound beam which corresponds to the quantity of outputted light $C_{OUT}$, the echo data of the respective voxels of the ultrasound beam are reflected, and the thus-obtained brightness value data is used as a brightness value P(x,y) for a pixel corresponding to the ultrasound beam. The brightness value data P(x,y) is sequentially stored in a predetermined address in the frame memory of the DSC 28 as the brightness value P(x,y) of the corresponding pixel.

Upon completion of processing the ultrasound beam as described above, the processing for a next ultrasound beam starts. When the above described processing is carried out for all the ultrasound beams, the brightness value data for the ultrasound beams are stored at predetermined addresses of the frame memory as brightness values at the corresponding respective pixels, from which a single frame of an ultrasound image for the three-dimensional region is produced. Thereafter, the brightness value data is read from the frame memory in the DSC 28 sequentially to display the ultrasound image on a display screen 42.

In addition, in this embodiment, the opacity $\alpha$ is determined in accordance with Equation (2), and the opacity adjustment coefficient $\beta$ in Equation (1) can be adjusted by the opacity adjuster 44 as described above. Accordingly, by appropriately adjusting the opacity adjuster 44, it is possible to adjust an emphasis on either the transparent effect or the stereoscopic effect of a stereoscopic ultrasound image, as well as the depth of a stereoscopic transparent image. Such adjustment can be carried out by adjusting an adjuster such as a dial or lever by an operator while observing the image displayed on a screen in real time.

(5) Advantage of the Ultrasound Image Processing Apparatus

The ultrasound image formed by the above-described ultrasound image processing apparatus is advantageous in diagnosing a living body, since it is formed into a three-dimensional surface image of an object such as an organ or a fetus or a three-dimensional transparent image capable of displaying the inside of the object like an X-ray image. Also, according to the ultrasound image processing apparatus, since the respective ultrasound beams emitted toward the three-dimensional region correspond to the respective pixels in an ultrasound image of the three-dimensional region, the number of the data to be processed for obtaining the ultrasound image can be reduced. Further, since ROM tables having data concerning a relationship between a value of echo data and an opacity and data concerning a relationship between a value of echo data and a transparency are used effectively, it is possible to produce such a three-dimensional ultrasound image on a real time base.

In the circuit configuration described above, each of the opacity operator 54 and the transparency operator 56 is formed from an individual ROM, respectively. However, in the above described apparatus using a binary digital circuit, it is possible to substitute these ROMs with a single common ROM. In this modification, an output of the common ROM is inverted to obtain a complement of 1 [one], and a transparency (1-α) is computed based on the output from the ROM. In more detail, a transparency (1-$α_i$) is obtained by subtracting from one [1] an opacity $α_i$ outputted from the α ROM.

Further, although in the ultrasound image processing apparatus described above Equation (4) uses one [1] as a predetermined end determination value K, it is also possible to have a means for varying this value K. If such a means is provided, it becomes possible to adjust the picture quality of an ultrasound image while observing the ultrasound image on a screen which is being produced in real time.

Furthermore, in the ultrasound image processing apparatus described above, the viewpoint from which an object is considered to be seen matches the point from which ultrasound beams are emitted toward the object. However, the ultrasound image processing apparatus of the present invention is in no way limited to such a structure. It is possible to set the viewpoint to a different point from the beam emitting point. In such a case, another algorithm which is similar to one performed in the X-ray CT apparatus is additionally carried out for producing a three-dimensional image considered to be viewed from the viewpoint.

DETAILED DESCRIPTION OF THE PREFERRED EMBODIMENTS

As stated in the above, the feature of the present invention is to provide an ultrasound image processing apparatus which is capable of simultaneously displaying a three-dimensional or stereoscopic ultrasound image of an object in a three-dimensional region and an associated tomographic image (B-mode image) of the object. The three-dimensional ultrasound image is produced in a real time base by the unique ultrasound image processing technique as described above, while the B-mode image has been being used from the past.

Hereinbelow, the present invention will be described in more details with reference to preferred embodiments thereof. In this regard, it should be noted that the following embodiments are described as examples when the present invention is applied to an ultrasound diagnostic apparatus. However, application of the present invention is not limited to such an ultrasound diagnostic apparatus.

Figure 8:
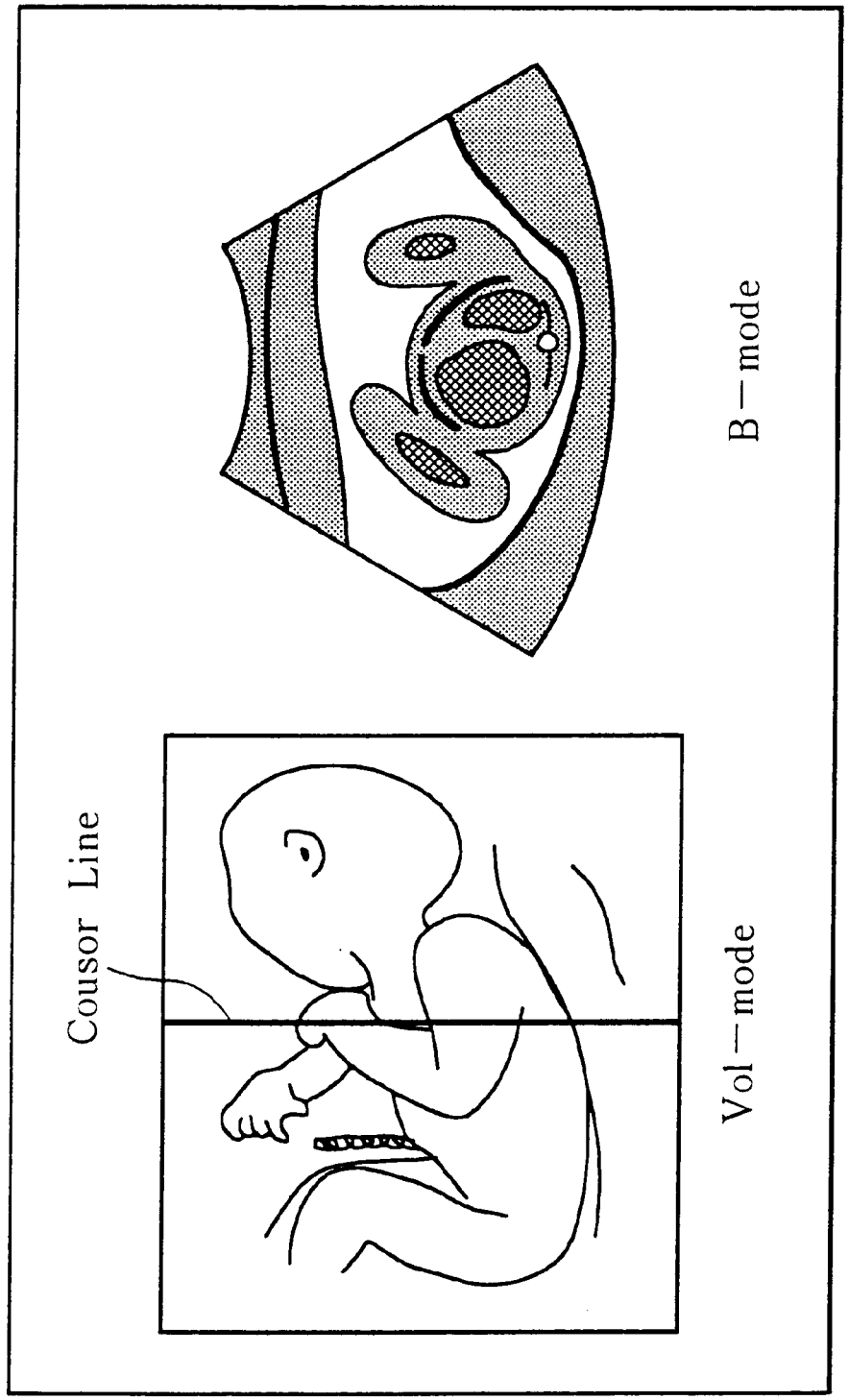
FIG. 8 is an illustration which shows an example of a display of the images provided according to a first embodiment of an ultrasound image processing apparatus according to the present invention, in which the stereoscopic image and the tomographic image (B-mode image) are both displayed simultaneously in a contrast manner.

FIG. 8 is an illustration which shows an example of the displayed images provided according to the ultrasound image processing apparatus of the first embodiment.

In the ultrasound image processing apparatus of the first embodiment, it is possible to display a stereoscopic ultrasound image (a stereoscopic surface image or a stereoscopic transparent image which are called as "Vol-mode image") of an object in a three-dimensional region produced in a real time base as well as an associated tomographic image (B-mode image) of the object on a screen simultaneously. Namely, as shown in FIG. 8, when the ultrasound image processing apparatus is used in an ultrasound diagnostic apparatus, a three-dimensional image (Vol-mode image) of an object (e.g. fetus) which is positioned in a three-dimensional region (e.g. a living body) and a B-mode image of the object (fetus) can be displayed on a single screen simultaneously in a contrast manner.

Further, in this first embodiment, there is another specific feature in which a position of a sectional plane for the object which is represented with the B-mode image can be designated freely on the displayed three-dimensional image. Namely, as shown in the drawing, it is possible to display a B-mode image of the object taken along a sectional plane which is determined by a line freely designated on the displayed three-dimensional image by means of a cursor.

In this regard, although both the images are displayed on the screen in the example shown in FIG. 8, these two images may be displayed on separate two screens, respectively. Further, it is also possible to construct the screen to be switchable by means of an appropriate switching means so as to be able to display either one of the images as necessary.

Figure 9:
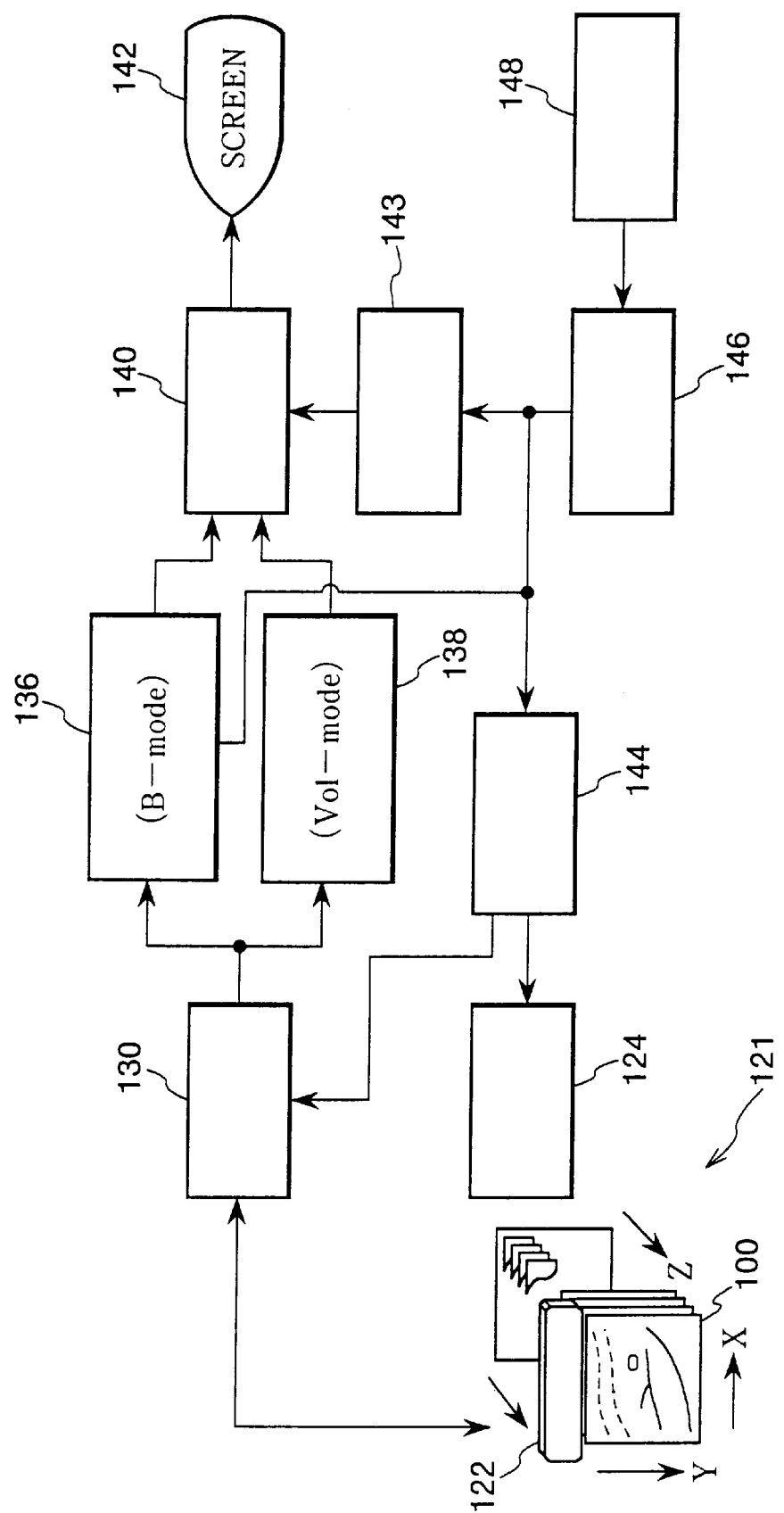
FIG. 9 is a block diagram which shows an overall construction of the ultrasound image processing apparatus of the first embodiment.

FIG. 9 is a block diagram which shows an overall structure of the ultrasound image processing apparatus of the first embodiment which is capable of displaying the stereoscopic ultrasound image together with the B-mode image simultaneously.

In FIG. 9, the reference numeral 122 denotes an ultrasound probe for acquiring data of a three-dimensional region. The ultrasound probe 122 is provided with an ultrasound transducer for transmitting and receiving ultrasound beams to and from the three-dimensional region. The ultrasound probe 122 and the transducer are driven and controlled by a scanning mechanism 124. As is the same as the example shown in FIG. 1, a linear array type ultrasound transducer is used in the ultrasound probe 122. However, it is of course possible to employ a convex type ultrasound transducer or the like. The ultrasound transducer performs electronic scanning (linear scanning or sector scanning), and with this result, a scanning plane 100 is formed in an X-Y plane as shown in FIG. 2 (A).

In FIG. 9, the reference numeral 130 denotes a transmission and reception section. The transmission and reception section 130 is provided for supplying a transmission signal to the ultrasound transducer to transmit ultrasound waves and then processing echo signals obtained based on echoes of the transmitted ultrasound waves which are received by the ultrasound transducer. Here, although not shown in the figure, the echo signals are amplified by an amplifier as is the same as the case shown in FIG. 1, and then the echo signals are logmatically amplified by a LOG amplifier. Then, the echo signals are fed to a tomographic image data producing section 136 and a stereoscopic image data producing section 138, respectively, after they have been A/D converted by an A/D converter not shown in the drawing.

As described above, the tomographic image data producing section 136 produces tomographic image data taken along a sectional plane which is freely designated on the displayed three-dimensional image with a cursor, so that this section functions as a B-mode image producing section. This B-mode image producing section 136 enables to produce a B-mode image taken along the sectional plane which is freely designated on the displayed three-dimensional image by the cursor line. Namely, the B-mode image is produced based on the echo data on the sectional plane. The B-mode image producing section 136 is composed of known structure and circuit.

The stereoscopic image data producing section 138 produces stereoscopic image data based on the principle as described above. Although not shown in the drawing, the stereoscopic image processor 138 includes circuits corresponding to the image generator 38 and the opacity adjuster 40 shown in FIG. 1.

The image processing section of the stereoscopic image data producing section 138 corresponds to the image processor 38 of the stereoscopic image data generator 37 shown in the block diagram of FIG. 1, and therefore it has a circuit configuration same as that shown in FIG. 7. Therefore, the detailed description of the stereoscopic image data producing section 138 is omitted.

Tomographic image data outputted from the tomographic image data producing section 136 and three-dimensional image data outputted from the stereoscopic image data producing section 138 are inputted into a display controlling section 140. The display controlling section 140 has a display image producing function and a combined image producing function. Specifically, this display controlling section 140 produces a single display image in which the three-dimensional stereoscopic image and the tomographic image (B-mode image) are combined side by side in a contrast manner as shown in FIG. 8, and further synthesises the cursor line which is fed from a cursor line data producing section 143 (described later in details) on the stereoscopic image.

Figure 10:
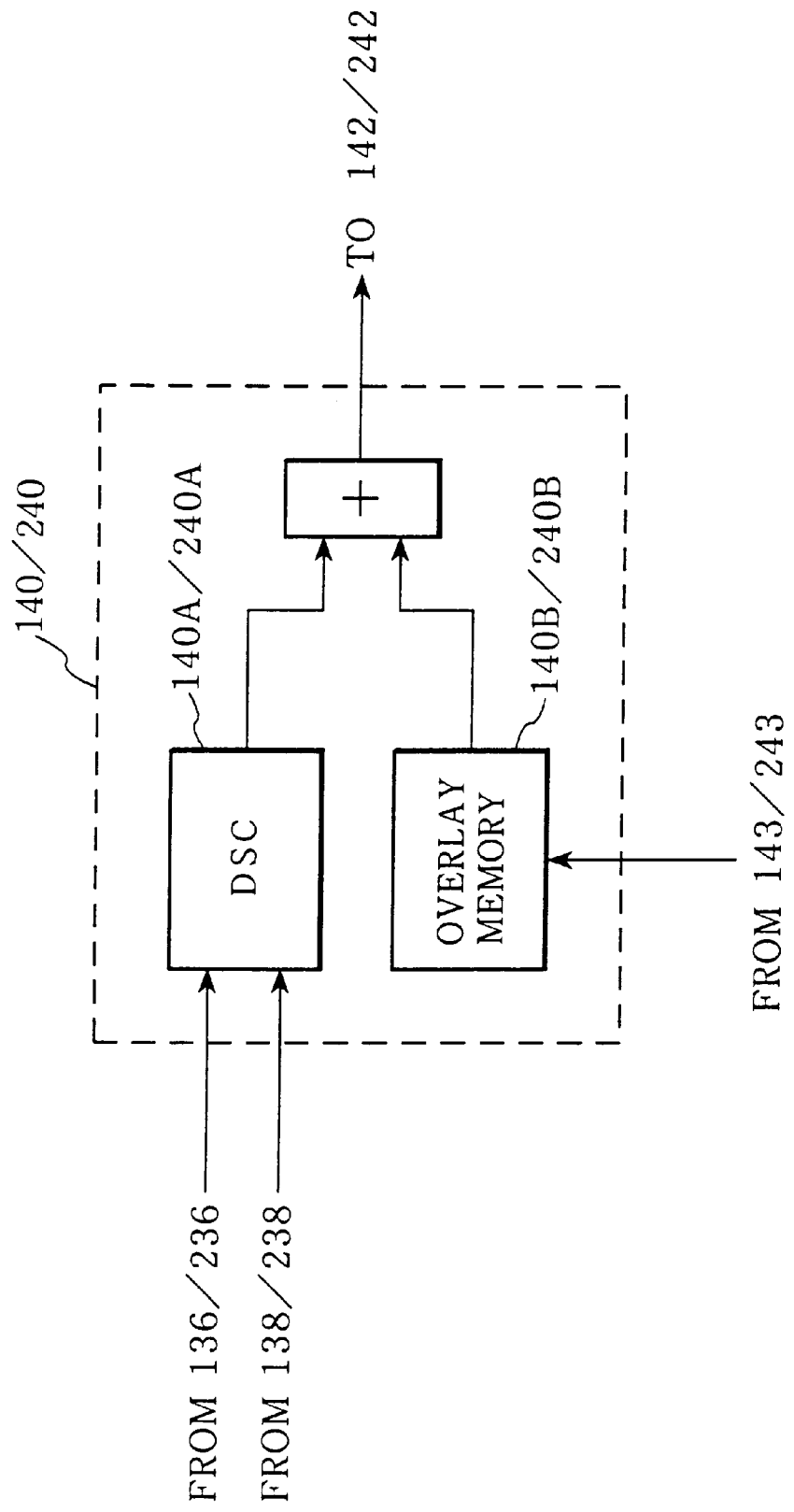
FIG. 10 is a block diagram which shows a construction of the display control section 140 of the first embodiment shown in FIG. 9.

In more details, as shown in FIG. 10, the display controlling section 140 includes a digital scan converter (DSC) 140A with a frame memory and an overlay memory 140B. The tomographic image data outputted from the tomographic image data producing section 136 and the three-dimensional stereoscopic image data outputted from the stereoscopic image data producing section 138 are inputted into the DSC 140A, and then written in predetermined addresses of the frame memory, respectively, to form a single frame image in which the two images are combined. Further, cursor line data outputted from the cursor line data producing section 143 is inputted into the overlay memory 140B, and the cursor line data is then ovrelaid on the stereoscopic image data in the frame memory.

Thus formed combined image data is D/A converted by a D/A converter (not shown) and then displayed on the screen 142 together with the cursor line.

In FIG. 9, the reference numeral 144 denotes a scanning control section which controls transmission and reception of the ultrasound waves through the transmission and reception section 130, and further controls the scanning mechanism 124 mechanically and erectronically.

The reference numeral 148 is a pointing device for freely designating a position of the sectional plane on the displayed three-dimensional stereoscopic image on the screen 142. Examples of such a pointing device include a trackball, a key board and a mouse and the like. The position of the sectional plane is designated by the pointing device, and the positional information of the position is inputted into a sectional plane position setting section 146 and then positional data of the position of the sectional plane is produced based on the information.

The sectional plane position setting section 146 outputs the positional data which indicates the position of the sectional plane with its address in the Z direction. In this connection, it should be noted that in this embodiment the direction of the cursor line is the same as the X direction (electronic scanning direction) shown in FIG. 2, and the sectional plane is set on the X-Y plane. Therefore, the position of the sectional plane can be represented by the information concerning the address in the Z direction.

The positional data of the sectional plane is inputted into the cursor line data producing section 143 described above, where cursor line image data is produced based on the positional data. As described above, the cursor line data is supplied to the overlay memory 140B in the display controlling section 140.

The positional data of the sectional plane is also supplied to the scanning control section 144 to move the ultrasound probe 122 to the position indicated by the positional data. The positional data of the sectional plane is further supplied to the tomographic image data producing section 136. In this way, it becomes possible to display a B-mode image taken along the sectional plane designated by the cursor line in real time together with the three-dimensional stereoscopic image simultaneously on the same screen as shown in FIG. 8.

According to the above construction, by designating a desired position of a sectional plane on the displayed stereoscopic image which is being produced in real time while observing thus produced displayed three-dimensional image, it is possible to display a B-mode image taken along the designated sectional plane together with the three-dimensional image simultaneously on the same screen. In this case, if the designated position of the sectional plane is moved by the pointing device, the B-mode image is also changed in real time into a B-mode image at a new position of the sectional plane.

In this embodiment, the designation of the position of the sectional plane for B-mode image may be carried out under the condition that the three-dimensional image displayed on the screen is being frozen. In this case, the positional data of the sectional plane is supplied to the scanning control section 144 from the sectional plane position setting section 146 to move the ultrasound probe 122 to the designated position relative to the object, at which echoes are acquired by the ultrasound probe 122 to produce a B-mode image based on the aquired echo data.

Figure 11:
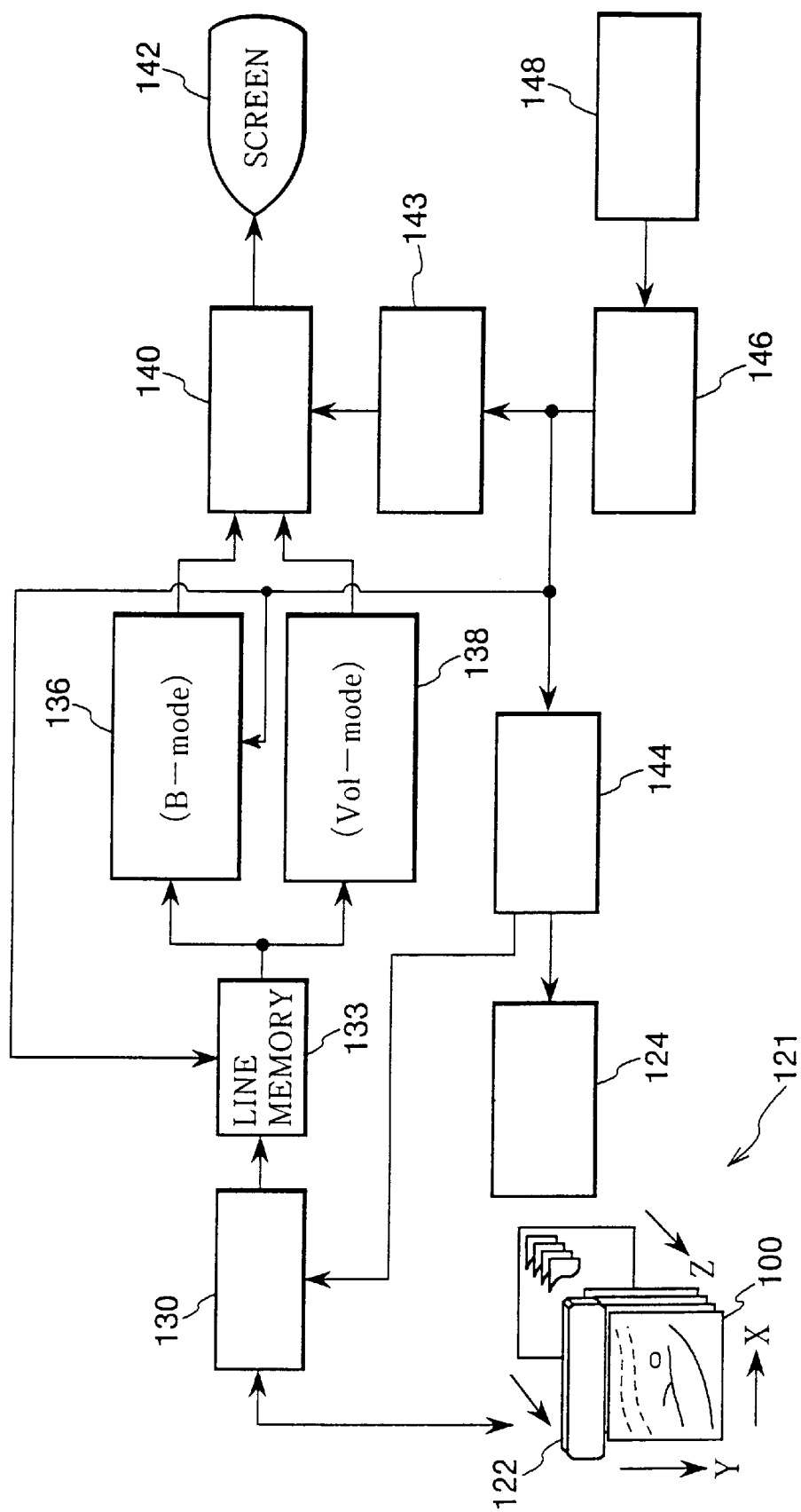
FIG. 11 is a block diagram which shows modification of the first embodiment shown in FIG. 9.

FIG. 11 shows a modification of the circuit configuration of the embodiment shown in FIG. 9. In this modification, a line memory 133 is additionally provided between the output of the transmission and reception section 130 and the inputs of the tomographic data producing section 136 and the stereoscopic image data producing section 138. The line memory 133 is provided for storing line data of the respective ultrasound beams received by the ultrasound transducer. In operation, line data of the respective ultrasound beams reflected from a three-dimensional region is successively stored in the line memory 133, and then a three-dimensional image is produced based on the data stored in the line memory 133.

In this modification, when a position of a sectional plane for B-mode image is designated on the displayed three-dimensional image, echo data for forming the B-mode image is read out from the data stored in the line memory 133. Therefore, in this modification, it is no longer necessary to move the ultrasound probe 122 to the designated position as was done in the embodiment shown in FIG. 9, so that a supply of the positional data of the sectional plane from the sectional plane position setting section 146 to the scanning control section 144 becomes unnecessary.

As described above, according to the ultrasound image processing apparatus of the first embodiment, by designating a desired position of a sectional plane for B-mode image on the displayed three-dimensional image, it is possible to produce a B-mode image at the designated sectional plane in real time, and it is also possible to display such a B-mode image together with the three-dimensional image simultaneously on the same screen. As a result, a diagnosd part of a patient can be observed through different images in real time, thereby effectiveness in diagnosis is improved and more reliable diagnosis can be performed.

Next, with reference to FIGS. 12 to 14, a second embodiment of the ultrasound image processing apparatus according to the present invention will be described.

Figure 12:
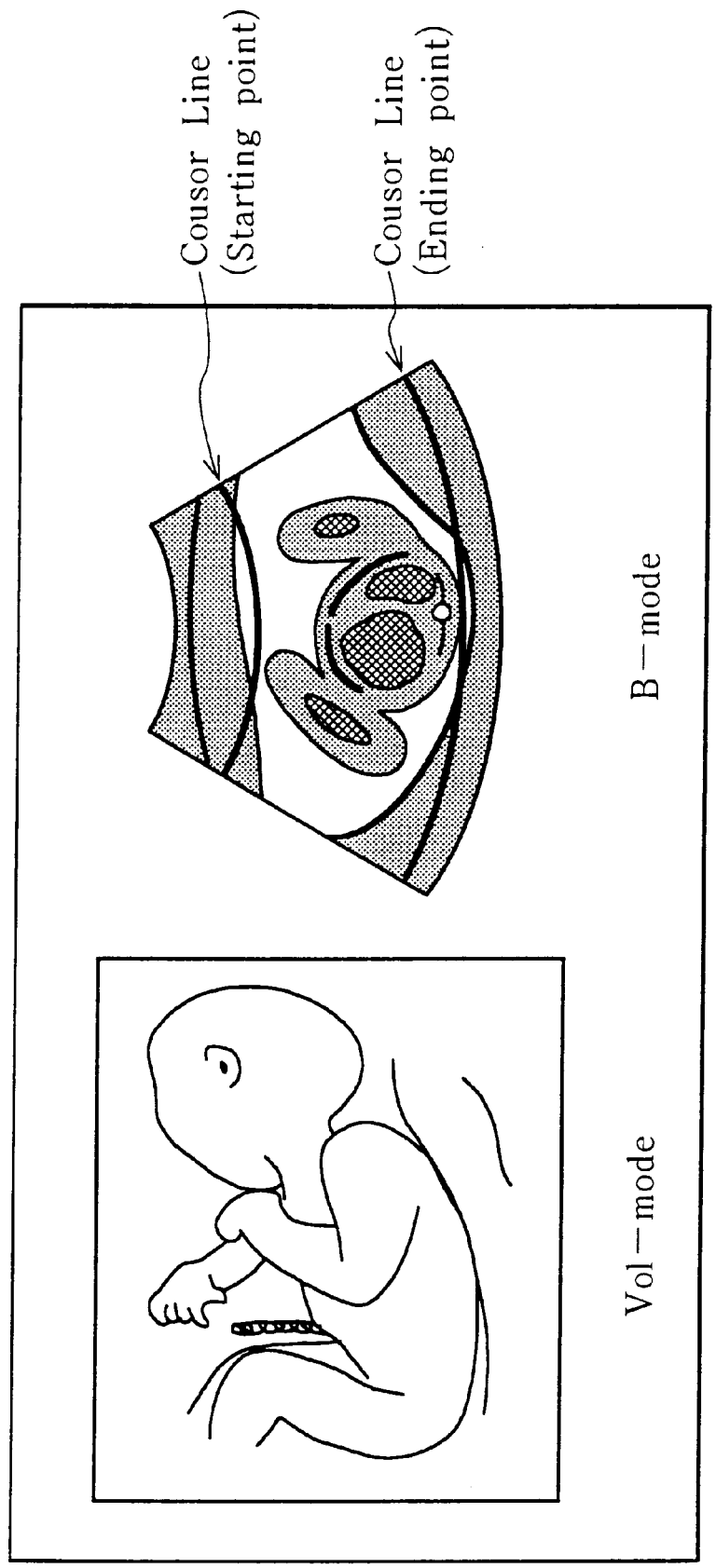
FIG. 12 is an illustration which shows an example of a display of the images provided according to a second embodiment of an ultrasound image processing apparatus according to the present invention, in which the three-dimensional image and the tomographic image (B-mode image) are displayed simultaneously in a contrast manner.

FIG. 12 is an illustration which shows an example of a displayed image provided according to the ultrasound image processing apparatus of the second embodiment.

As is the same with the first embodiment described above, in the ultrasound image processing apparatus of the second embodiment, it is also possible to display on a screen a three-dimensional ultrasound image (a stereoscopic surface image or a three-dimensional transparent image which is called as "Vol-mode image") of an object in a three-dimensional region produced in a real time base as well as an associated tomographic image (B-mode image) of the object. Namely, as shown in FIG. 12, when the ultrasound image processing apparatus is used in an ultrasound diagnostic apparatus, a three-dimensional image (Vol-mode image) of an object (e.g. fetus) which is positioned in a three-dimensional region (e.g. a living body) and a B-mode image of the object (fetus) can be displayed on a single screen simultaneously in a contrast manner.

Further, in this second embodiment, there is another specific feature which is developed in order to solve a problem pointed out by a user of an ultrasound diagnostic apparatus to which the ultrasound image processing apparatus described above is applied. Namely, when observing an internal organ or the like by the ultrasound diagnostic apparatus, there is a case that an observation is disturbed due to other organ which is positioned in front of or in rear of the organ to be observed, since such other organ appears in the three-dimensional image displayed in the screen. In more concrete, for example, when observing a fetus, a placenta which is positioned at a place closer to the body surface rather than the fetus is likely to appear on the displayed three-dimensional image. In view of the problem, the feature of this embodiment is directed to the improvement in which a data processing range having echo data for producing a three-dimensional image can be freely designated in the three-dimensional region based on the displayed B-mode image.

In this regard, it is to be noted that although in the example shown in FIG. 12 both the images are displayed on the same screen, these two images may be displayed on separate two screens, respectively. Further, it is also possible to construct the screen to be switchable by means of an appropriate switching means so as to be able to display either one of the images as necessary.

Figure 13:
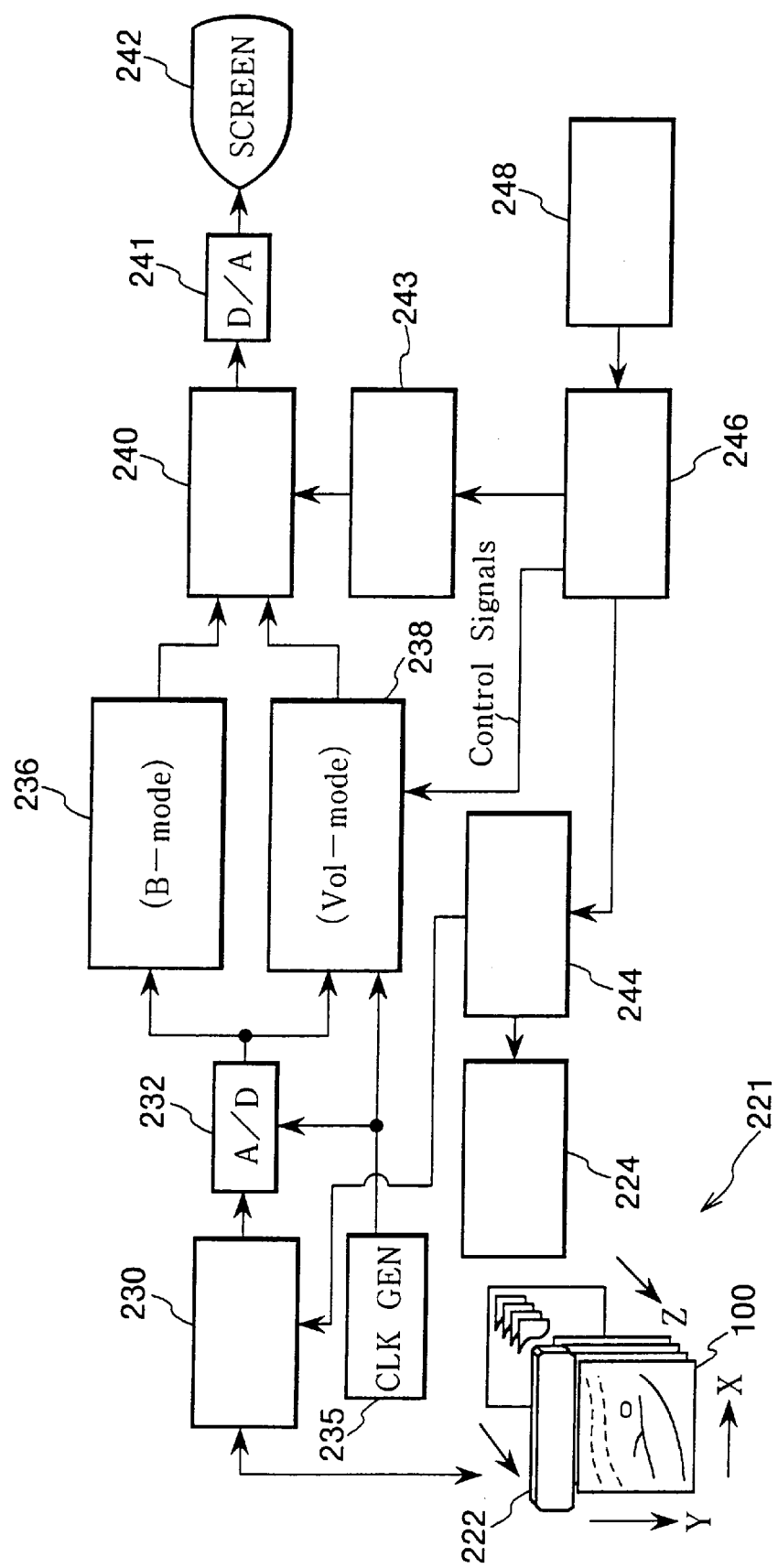
FIG. 13 is a block diagram which shows an overall construction of the ultrasound image processing apparatus of the second embodiment.

FIG. 13 is a block diagram which shows an overall structure of the ultrasound image processing apparatus of the second embodiment which is capable of displaying the three-dimensional ultrasound image together with the B-mode image simultaneously.

In FIG. 13, the reference numeral 222 denotes an ultrasound probe for acquiring echoes from a three-dimensional region. As is the same with the first embodiment, the ultrasound probe 222 is provided with an ultrasound transducer for transmitting and receiving ultrasound beams to and from a three-dimensional region. The ultrasound probe 222 and the transducer are driven and controlled by a scanning mechanism 224. As is the same as the example shown in FIG. 1, a linear array type ultrasound transducer is used as the ultrasound transducer of this embodiment. However, it is of course possible to employ a convex type ultrasound transducer or the like. The ultrasound transducer is electronically scanned (linear scanning or sector scanning), and with this result, a scanning plane 100 is formed in an X-Y plane as shown in FIG. 2 (A).

In FIG. 13, the reference numeral 230 denotes a transmission and reception section. The transmission and reception section 230 is provided for supplying a transmission signal to the ultrasound transducer to transmit ultrasound waves and then processing echo signals obtained based on echoes of the transmitted ultrasound waves which are received by the ultrasound transducer. Here, although not shown in the figure, the echo signals are amplified by an amplifier and then logmatically amplified by a LOG amplifier in the same way as the apparatus shown in FIG. 1. Then, the echo signals are fed to a tomographic image data producing section 236 and a three-dimensional image data producing section 238 after they are A/D converted by an A/D converter 232, respectively. In this case, it should be noted that a sampling clock generated in a clock generator 235 is supplied to the A/D converter 232 and the stereoscopic image data producing section 238.

As is the same with the first embodiment described above, the tomographic image data producing section 236 produces tomographic image data taken along a sectional plane which is freely designated on the displayed three-dimensional image with a cursor line, so that this section 236 functions as a B-mode image producing section. This B-mode image producing section 236 produces based on a part of the obtained echo data a B-mode image taken along the sectional plane which is freely designated on the displayed three-dimensional image by the cursor line. The B-mode image producing section 236 is composed of known structure and circuit.

The stereoscopic image data producing section 238 produces three-dimensional image data based on the obtained echo data according to the principle as described above. Although not shown in the drawing, the three-dimensional image data producing section 238 includes a circuit (Vol-mode image data processor) shown in FIG. 14 described later and an opacity adjuster which is the same as one shown in FIG. 1 with the reference numeral 44.

In this second embodiment, a data processing range containing echo data to be processed for producing a stereoscopic image can be freely designated by user on the displayed B-mode image, and the three-dimensional image is produced based on the echo data obtained from the designated data processing range.

Tomographic image data outputted from the tomographic image data producing section 236 and stereoscopic image data outputted from the three-dimensional image data producing section 238 are inputted into a display controlling section 240. This display controlling section 240 has a display image production function and an image combining function. Specifically, this display controlling section 240 produces a single display image in which the three-dimensional image and the tomographic image (B-mode image) are incorporated and combined side by side in a contrast manner as shown in FIG. 12, and further synthesizes the cursor line which is produced based on the data fed from a cursor line data producing section 243 (described later in details) on the tomographic image.

As is the same with the display controlling section 140 of the first embodiment, the display controlling section 240 of this second embodiment has the same structure as shown in FIG. 10. Specifically, the display controlling section 240 includes a digital scan converter (DSC) 240A with a frame memory and an overlay memory 240B. The tomographic image data outputted from the tomographic image data producing section 236 and the stereoscopic image data outputted from the three-dimensional image data producing section 238 are inputted into the DSC 240A, and then written in predetermined addresses of the frame memory, respectively, to form a single frame image in which the two images are combined. Further, cursor line data outputted from the cursor line data producing section 243 is inputted into the overlay memory 240B, and the cursor line data is then overlaid on the tomographic image data read out from the frame memory.

The output from the display controlling section 240 is fed to a display (screen 242) after having been A/D converted by a D/A converter 241, and the combined image is displayed on the screen 242.

In FIG. 13, the reference numeral 244 denotes a scanning control section which controls transmission and reception of the ultrasound waves through the transmission and reception section 230, and further controls the scanning mechanism 224 mechanically and electronically.

The scanning control section 244 also has a function that controls ultrasound pulse transmission repetition frequency (PRF). Namely, when an ending position signal which indicates an ending point of the data processing range is received from a data processing range setting section 246 (described later in more detail), the scanning control section 244 adjusts ultrasound pulse transmission repetition frequency (PRF) depending on the position of the ending point, if necessary. Specifically, the scanning control section 244 sets a pulse transmission repetition frequency (PRF) which is suitable for the time required for transmission and reception of an ultrasound wave between the transducer of the ultrasound probe 222 and the ending point. If necessary, an appropriate certain margin time may be added thereto.

The reference numeral 248 is a pointing device for freely designating a starting point (starting line) or an ending point (ending line) or both points (lines) which define a data processing range including echo data to be processed for producing a three-dimensional image, on the tomographic image being displayed on the screen 242. Examples of such a pointing device 248 include a trackball, a key board and a mouse and the like. The positions of the starting point and/or the ending point determined by the pointing device 248 are inputted into the data processing range setting section 246 in the form of positional information. The data processing range setting section 246 produces positional data of the starting point and the ending point based on the information and further produces a control signal which indicates the data processing range.

The data processing range setting section 246 outputs the positional data which indicates the starting point and/or the ending point to the cursor line data producing section 243. Further, the data processing range setting section 246 also outputs to the stereoscopic image data producing section 238 control signals for determining the data processing range. In addition, the data processing range setting section 246 also outputs to the scanning control section 244 the data which indicates the starting point and/or the ending point, as necessary.

The cursor line data producing section 243 produces cursor line data for the starting line and/or the ending line such as those shown in FIG. 12, based on the positional data which are fed from the data processing range setting section 246. Thus produced cursor line data are overlaid onto the tomographic image data as described above.

In this connection, it should be noted that the tomographic image corresponds to an image on X-Y plane in FIG. 2A. Therefore, it is possible to obtain a tomographic image at a desired position by designating a Z coordinate of the desired position. For this reason, designation of the starting point and/or the ending point can be carried out on a displayed tomographic image at the desired position by using the pointing device 248 while moving the cursor freely on the displayed tomographic image.

As shown in FIG. 12, when a tomographic image is a sector scan B-mode image, the cursor lines that represent the depth along the ultrasound beam projecting direction are shown as arched lines. Of course, when an electronic linear scanning is carried out by the ultrasound probe 222 as shown in FIG. 2, the cursor lines are shown by straight lines.

In this second embodiment as described above, the starting point (line) and the ending point (line) are set so as to have the same depth in the beam projecting direction. However, it is possible to change the depth of each point in each of the ultrasound beams. Further, this data processing range can be defined by using a closed line such as an ellipse shape or a square shape or free-form curves.

According to the second embodiment having the above construction, if an appropriate data processing range for producing a three-dimensional image is determined on the tomographic image which is being displayed in real time, a stereoscopic image formed from echo data contained in the data processing range can also be produced and displayed on the same screen together withe the tomographic image in a real time base. Further, it is also possible to designate such a data processing range on a B-mode image under the condition that only the B-mode image is being displayed on a screen. In this case, it is also possible to produce a three-dimensional image based on echo data contained in the data processing range and display such a three-dimensional image together with the B-mode image.

Hereinbelow, an example of a circuit configuration of the stereoscopic image data producing section 238 of the second embodiment will be described with reference to FIGS. 13 and 14.

Figure 14:
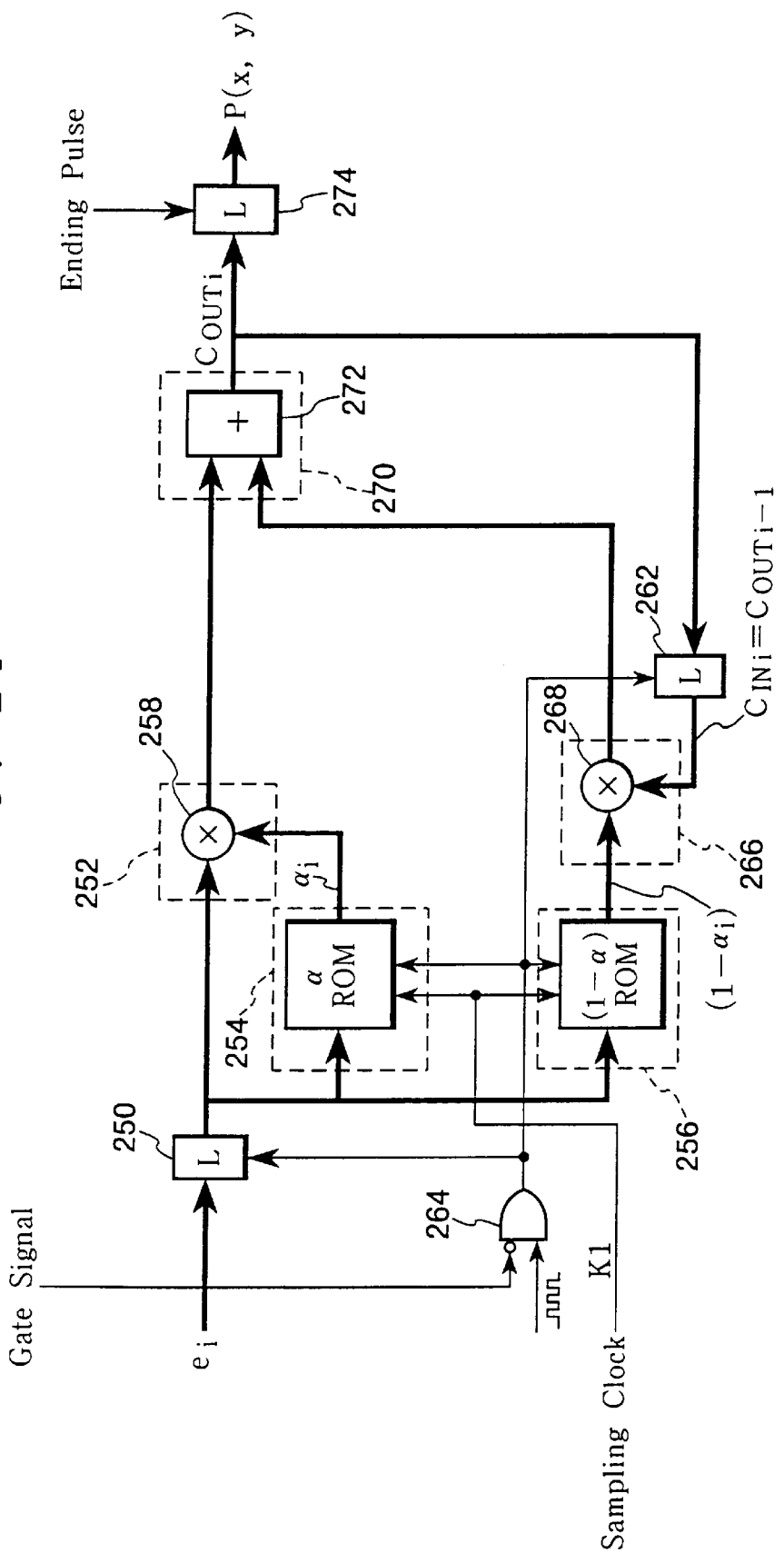
FIG. 14 is a block diagram which shows a construction of the three-dimensional stereoscopic image data processing unit of the second embodiment.

FIG. 14 is an illustration which shows an example of the circuit configuration of the Vol-mode image data processor in the stereoscopic image data producing section 238. This circuit configuration is similar to that shown in FIG. 7 excepting that the end determination section 77 shown in FIG. 7 is removed. Instead thereof, in this embodiment, the control signals supplied from the data processing range setting section 246 are inputted.

Specifically, as is the same with the case shown in FIG. 7, normalized echo data $e_i$ at an i-th voxel 20 which has already been A/D converted is sequentially inputted to the Vol-mode image data processor. The inputted echo data $e_i$ is first latched by a latch circuit 250, and then it is inputted to a luminescence quantity operator 252, an opacity operator 254 and a transparency operator 256, respectively. The luminescence quantity operator 252 comprises a multiplier 258. The multiplier 258 calculates the luminescence quantity as a product $e_i \times \alpha_i$ by multiplying normalized echo data $e_i$ by an opacity $\alpha_i$ at each voxel 20. In this embodiment, the opacity operator 254 comprises an $\alpha$ ROM. The $\alpha$ ROM includes a table having data concerning a corresponding relationship between the normalized echo data e and the opacity $\alpha$. Similarly, the transparency operator 256 comprises a $(1-\alpha)$ ROM, which includes a table having data concerning a corresponding relationship between the normalized echo data e and the transparency $(1-\alpha)$.

Consequently, when the normalized echo data $e_i$ of an i-th voxel 20 is inputted into the opacity operator 254, the opacity operator 254 outputs opacity $\alpha_i$ at the voxel 20. Further, when the normalized echo data $e_i$ of the i-th voxel 20 is inputted into the transparency operator 256, the transparency operator 256 outputs transparency $(1-\alpha_i)$ at the voxel 20.

The opacity operator 254, the transparency operator 256, the latch circuit 250 and the latch circuit 262 are all supplied via an AND gate 264 with a sampling clock provided by the clock generator 235 shown in FIG. 13. This sampling clock is also supplied to the A/D converter 232 shown in FIG. 13 for an A/D conversion. As a result, this sampling clock causes other circuits shown in FIG. 14 to operate in synchronization with the A/D converter 232. This enables normalized echo data e at each sampling point, that is, normalized echo data e at each voxel 20, to be processed sequentially.

The output of the transparency operator 256 is supplied to a transmitted light quantity operator 266 which comprises a multiplier 268. The multiplier 268 multiplies a transparency $(1-\alpha_i)$ outputted from the transparency operator 256 by a quantity of outputted light $C_{OUTi-1}$ of the immediately preceding (i-1)-th voxel 20 latched by latch circuit 262. Namely, the transmitted light operator quantity 266 outputs a quantity of transmitted light as a product $C_{INi} \times (1-\alpha_i)$ by multiplying a quantity of inputted light $C_{INi}$ of the i-th voxel by a transparency $(1-\alpha_i)$ at the voxel 20.

A light quantity adder 270 which is constructed from an adder 272 adds the quantity of luminescence to the quantity of transmitted light based on Equation (3) described above with reference to FIG. 6, to output the sum as a quantity of outputted light $C_{OUTi}$ at the i-th voxel 20. The quantity of outputted light $C_{OUTi}$ outputted from the light quantity adder 270 is supplied to a latch circuit 274 having a gate function and the latch circuit 262, respectively. That is, the quantity of outputted light at an i-th voxel 20 is fed back via the latch circuit 262 to the transmitted light quantity operator 266 for computing a quantity of outputted light at an immediately succeeding (i+1)-th voxel 20.

As shown in FIG. 13, the control signals fed from the data processing range setting section 246 are inputted into this the Vol-mode image data processor. The control signals include a gate signal and an ending pulse. The gate signal is used to determine a voxel data processing range, that is a range between the starting point and the ending point for an ultrasound beam. This gate signal is inputted into the AND gate 264. When the gate signal is inputted, the AND gate 264 allows the sampling clock to pass through only for the voxel data processing range. On the other hand, the ending pulse is inputted into the latch circuit 274. When this ending pulse is inputted, the quantity of outputted light $C_{OUTi}$ which is outputted from the light quantity adder 270 and latched in the latch circuit 274 is fed to the display controlling section 240. The quantity of outputted light $C_{OUTi}$ becomes the brightness value data of the ultrasound beam which corresponds to a brightness value P(x,y) at a pixel in an ultrasound image on a display screen. In this case, the quantity of outputted light $C_{OUTi}$ may be correlated with hue of the displayed image.

As described above, according to the circuit configuration shown in FIG. 14, a series of the voxels beginning from the start voxel are sequentially processed along the projecting direction of the ultrasound beam in each of the received ultrasound beams. The processing described above is carried out for each voxel, and the output from the light quantity adder 270 is used for processing an immediately succeeding voxel. In this way, processing for the voxels of the ultrasound beam are successively carried out, and the quantity of outputted light $C_{OUT}$ of the last voxel is used as a brightness value data at a pixel on an ultrasound image which corresponds to the ultrasound beam. After completion of processing for one ultrasound beam, a series of the voxels in the next ultrasound beam are processed in the same way. When all the ultrasound beams are processed in this way, that is when all the echo data are processed, three-dimensional ultrasound image data for one frame is stored in the frame memory of the display controlling section 240. Such ultrasound image data is then read out from the frame memory and an ultrasound image based on the ultrasound image data is displayed on the screen 242.

In this connection, please note that the circuit configuration shown in FIG. 14 is an example which is used when both the starting point and the ending point are designated on the displayed B-mode image. In a case where only a starting point is designated on the B-mode image, it is necessary to further provide an end determination circuit which determines a point of time when cumulative value of the opacity $\alpha$ reaches one [1] or a point of time when the last voxel is processed. The end determination circuit can be constructed from a circuit similar to the end determination section 77 shown in FIG. 7.

Further, in the circuit configuration shown in FIG. 14, the opacity $\alpha$ is determined in accordance with Equation (1) described above with reference to FIG. 4, and the opacity adjustment coefficient $\beta$ in Equation (1) can be adjusted by an opacity adjuster which is not shown in this figure but it is shown in FIG. 1 and FIG. 7 with the reference numeral 44. Accordingly, by appropriately adjusting the opacity adjuster, it is possible to adjust an emphasis on either the transparent effect or the stereoscopic effect of a three-dimensional ultrasound image, as well as the depth of a three-dimensional transparent image.

As described above, according to the ultrasound image processing apparatus of the second embodiment, a data processing range from which a three-dimensional image is to be produced can be freely designated on the displayed B-mode image. As a result, it becomes possible to improve quality of a displayed ultrasound image, namely it becomes possible to provide a stereoscopic ultrasound image which is not affected by obstructions outside the data processing rage, that is existing in front of or in rear of a part to be diagnosed. In addition, such a designation of the data processing range can be carried out easily on the displayed B-mode image.

Further, according to the ultrasound image processing apparatus of the second embodiment, it is possible to improve a frame rate, that is a displaying speed, by appropriately changing ultrasound pulse transmission repetition frequency (PRF) depending on the data processing range from which echo data is taken out for producing the stereoscopic image.

Specifically, in this embodiment, an end of volume rendering processing can be designated freely for each ultrasound beam as described above. This means that it is sufficient for transmission and reception of the ultrasound wave to be carried out within a range between the transducer and the position of the ending point that is the last voxel, so that transmission pulse repetition frequency (PRF) can be increased. This means that a frame rate of a display image can also be increased. With this result, it becomes possible to display a three-dimensional ultrasound image (Vol-mode image) with a higher frame rate. For example, if an ending point (a position of the last voxel) is set at a position half of respective ultrasound beams projected toward a three-dimensional region, a frame rate can be twice in comparison with a frame rate in the case where all the data along the ultrasound beams were processed. As a result, a Vol-mode image can be produced in a half time.

In the above described embodiments, the ultrasound image processing apparatus according to the present invention is applied to an ultrasound diagnostic apparatus, and the examples are made with reference to the cases where the ultrasound diagnostic apparatus is used for diagnosing a fetus. However, the ultrasound apparatus according to the present invention is also suitable for diagnosing other parts of a living body, for example, a circulatory system such as a blood vein, as well as organs such as the kidney and the bladder.

Furthermore, if the present invention is applied to fault detectors, sonar (devices), and fish school detectors and the like, it becomes possible to provide a unique ultrasound image never obtainable by conventional apparatuses. Namely, a three-dimensional transparent image of an object or a three-dimensional surface image of the object is freely selectable as necessary and a tomographic image such as a B-mode image can be displayed simultaneously together with the three-dimensional image.

Moreover, in the embodiments described above, ultrasound waves are utilized to produce a three-dimensional image. However, the concept of the present invention does not eliminate use of other beams such as an electromagnetic wave. Therefore, it should be noted that the term "beam" in this application includes other beams besides ultrasound beam. As an example of the application using electromagnetic waves includes a radar or the like.

Finally, although this invention has been described in its preferred embodiments with a certain degree of particularity, it is to be understood that the present disclosure of the preferred embodiments can be changed in details of construction and that the combination and arrangement of parts may be changed without departing from the spirit and the scope of this invention as hereinafter claimed.

What is claimed is:

1. An ultrasound image processing apparatus, comprising:
    (a) an ultrasound transducer for sequentially emitting ultrasound beams toward a three-dimensional region containing an object and receiving respective echoes of said ultrasound beams;
    (b) three-dimensional image data producing means for producing in a substantially real time base three-dimensional image data of said object in said three-dimensional region based on echo data obtained from the echoes of said ultrasound beams;
    (c) tomographic image data producing means for producing tomographic image data of a part of said object based on the echo data; and
    (d) display means which can simultaneously display a three-dimensional image of the object formed from the three-dimensional image data and a tomographic image of the object formed from the tomographic image data.

2. The ultrasound image processing apparatus as claimed in claim 1, wherein said three-dimensional image includes a three-dimensional surface image of the object or a three-dimensional transparent image of the object.

3. The ultrasound image processing apparatus as claimed in claim 1, wherein said display means includes a single display on which said three-dimensional image and said tomographic image can be displayed simultaneously in a contrast manner.

4. The ultrasound image processing apparatus as claimed in claim 3, wherein said display means is constructed so as to be switchable between a first mode in which said three-dimensional image and said tomographic image are both displayed simultaneously, a second mode in which said three-dimensional image is displayed, and a third mode in which said tomographic image is displayed.

5. The ultrasound image processing apparatus as claimed in claim 1, further comprising a sectional plane setting means for setting a sectional plane for said object along a desired line designated on said displayed three-dimensional image, wherein said tomographic image data producing means produces the tomographic image data based on the echo data obtained from the sectional plane.

6. The ultrasound image processing apparatus as claimed in claim 5, further comprising a cursor line displaying means for displaying a cursor line which represents the position of the sectional plane on said three-dimensional image displayed on said display means.

7. The ultrasound image processing apparatus as claimed in claim 6, wherein the direction of said cursor line corresponds to an electronic scanning plane produced by electronic scanning performed by said ultrasound transducer.

8. The ultrasound processing apparatus as claimed in claim 1, further comprising means for determining, based on said displayed tomographic image, a range of the echo data to be processed, wherein said three-dimensional image data producing means produces said three-dimensional image data based on the echo data obtained from said range.

9. The ultrasound image processing apparatus as claimed in claim 8, wherein said range determining means is constructed so as to set one of a starting point and an ending point of the range along the ultrasound beam direction.

10. The ultrasound image processing apparatus as claimed in claim 8, wherein said range determining means is constructed so as to set both the starting point and ending point of the range along the ultrasound beam direction.

11. The ultrasound image processing apparatus as claimed in claim 8, further comprising means for displaying on said displayed tomographic image cursor lines which represent the range determined by said range determining means.

12. The ultrasound image processing apparatus as claimed in claim 8, wherein pulse repetition frequency (PRF) of the ultrasound beams is adjusted depending on the depth of the ending point of the range when the range is determined by said range determining means.

13. An ultrasound image processing apparatus, comprising:
    (a) means for emitting ultrasound beams toward a three-dimensional region containing an object and receiving echoes of the ultrasound beams;
    (b) three-dimensional image producing means for producing a three-dimensional image of the object in the three-dimensional region based on echo data obtained from the echoes of the ultrasound beams;
    (c) tomographic image producing means for producing a tomographic image along a sectional plane in the object based on a part of the echo data, said sectional plane being designated at a desired portion on said three-dimensional image;

(d) means of simultaneously displaying both said three-dimensional image and said tomographic image on a display in a contrast manner.

14. The ultrasound image processing apparatus as claimed in claim 13, wherein the sectional plane from which said tomographic image is produced is indicated on said displayed three-dimensional image.

15. An ultrasound image processing apparatus, comprising:

(a) means for transmitting ultrasound beams toward a three-dimensional region containing an object and receiving echoes of the ultrasound beams;

(b) tomographic image producing means for producing a tomographic image along a sectional plane of the object based on echo data obtained from the echoes of the ultrasound beams;

(c) three-dimensional image producing means for producing a three-dimensional image of a predetermined range in said three-dimensional region based on the echo data obtained from the range, said range being determined based on said tomographic image; and (d) means for simultaneously displaying both said three-dimensional image and said tomographic image on a display in a contrast manner.

16. The ultrasound image processing apparatus as claimed in claim 15, wherein the range having the echo data from which said three-dimensional image is to be produced is indicated on said displayed tomographic image.

17. A method of forming and displaying ultrasound images, comprising the steps of:

(a) transmitting ultrasound beams toward an object in a three-dimensional region and receiving echoes of the ultrasound beams;

(b) producing a three-dimensional image data of said object in said three-dimensional region in a real time base based on echo data obtained from the echoes of the received ultrasound beams;

(c) producing a tomographic image data of said object based on a part of the echo data of the received ultrasound beams; and (d) displaying a three-dimensional image which is formed based on the three-dimensional image data and a tomographic image which is formed based on the tomographic image data on a single display simultaneously such that these images are contrasted with each other.

18. The method of forming and displaying ultrasound images as claimed in claim 17, further comprising a step of setting a sectional plane of said object at a desired portion on said displayed three-dimensional image, wherein said tomographic image is formed from the echo data obtained from the sectional plane.

19. The method of forming and displaying ultrasound images as claimed in claim 17, further comprising a step of determining a range containing echo data to be processed based on said displayed tomographic image, wherein said three-dimensional image is produced from the echo data obtained from said range.

20. A method of diagnosing a living body using ultrasound images, comprising the steps of:

(a) transmitting ultrasound beams toward a three-dimensional region of a living body and receiving echoes of the transmitted ultrasound beams;

(b) producing a three-dimensional image data of an object in said three-dimensional region in a real time base based on echo data obtained from the echoes of the ultrasound beams;

(c) producing a B-mode image along a sectional plane of the object based on a part of the echo data; and (d) displaying said three-dimensional image and said B-mode image simultaneously on a single screen in a contrast manner, thereby diagnosing the object based on the displayed images.

* * * * *

UNITED STATES PATENT AND TRADEMARK OFFICE
CERTIFICATE OF CORRECTION

PATENT NO. : 5,911,691
DATED : June 15, 1999
INVENTOR(S) : Mochisuki et al.

It is certified that error appears in the above-identified patent and that said Letters Patent is hereby corrected as shown below:

Column 5,
Line 22, "stereoscopic" should read -- three-dimensional --.

Column 10,
Line 41, "Couti-1 an (i-l)-th" should read -- Couti-1 of an (i-l)-th --.

Column 16,
Line 36, "displaying the stereoscopic" should read -- displaying the three-dimensional or stereoscopic --.

Column 17,
Lines 33, 44 and 63, "three-dimensional stereoscopic" should read -- three-dimensional or stereoscopic --.

Column 18,
Line 26, "three-dimensional stereoscopic" should read -- three-dimensional or stereoscopic --.

Column 22,
Line 41, "stereoscopic" should read -- three-dimensional --.

Column 24,
Line 56, "stereoscopic" should read -- three-dimensional --.

Signed and Sealed this

Twenty-third Day of September, 2003

JAMES E. ROGAN
*Director of the United States Patent and Trademark Office*